(12) United States Patent
Kim et al.

(10) Patent No.: US 8,934,103 B2
(45) Date of Patent: Jan. 13, 2015

(54) QUANTITATIVE PHASE MICROSCOPY FOR LABEL-FREE HIGH-CONTRAST CELL IMAGING

(71) Applicant: General Electric Company, Schenectady, NY (US)

(72) Inventors: Evgenia Mikhailovna Kim, Ballston Lake, NY (US); Siavash Yazdanfar, Niskayuna, NY (US); Dmitry Vladimirovich Dylov, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 62 days.

(21) Appl. No.: 13/663,069

(22) Filed: Oct. 29, 2012

(65) Prior Publication Data

US 2013/0286400 A1     Oct. 31, 2013

Related U.S. Application Data

(63) Continuation-in-part of application No. 13/335,748, filed on Dec. 22, 2011, now Pat. No. 8,693,000.

(51) Int. Cl.
| | |
|---|---|
| *G01B 9/02* | (2006.01) |
| *G02B 21/00* | (2006.01) |
| *G01B 9/04* | (2006.01) |
| *G01N 21/45* | (2006.01) |
| *G02B 21/14* | (2006.01) |
| *G01B 11/06* | (2006.01) |

(52) U.S. Cl.
CPC ............... *G01B 9/0209* (2013.01); *G01B 9/04* (2013.01); *G01N 21/45* (2013.01); *G02B 21/14* (2013.01); *G01B 11/0675* (2013.01)
USPC .......................................... 356/450; 359/370

(58) Field of Classification Search
CPC .... G01B 9/02028; G01B 9/0209; G01B 9/04; G01N 33/48; G02B 21/0052; G02B 21/0056
USPC .......................... 356/450, 456; 359/370, 371
See application file for complete search history.

(56) References Cited

U.S. PATENT DOCUMENTS

| | | | |
|---|---|---|---|
| 3,658,405 A | 4/1972 | Pluta | |
| 5,241,364 A | 8/1993 | Kimura | |

(Continued)

FOREIGN PATENT DOCUMENTS

| | | | |
|---|---|---|---|
| JP | 2011033406 A | * | 2/2011 |
| WO | 2013095282 A2 | | 6/2013 |
| WO | 2013187833 A1 | | 12/2013 |

OTHER PUBLICATIONS

Daaboul et al., "LED-Based Interferometric Reflectance Imaging Sensor for Quantitative Dynamic Monitoring of Biomolecular Interactions", Biosensors and Bioelectronics, pp. 1-7, 2010.

(Continued)

*Primary Examiner* — Michael A Lyons
(74) *Attorney, Agent, or Firm* — Fletcher Yoder, P.C.

(57) ABSTRACT

Systems and methods described herein employ multiple phase-contrast images with various relative phase shifts between light diffracted by a sample and light not diffracted by the sample to produce a quantitative phase image. The produced quantitative phase image may have sufficient contrast for label-free auto-segmentation of cell bodies and nuclei.

20 Claims, 14 Drawing Sheets

(56) References Cited

U.S. PATENT DOCUMENTS

| | | | |
|---|---|---|---|
| 5,260,569 A | 11/1993 | Kimura | |
| 5,426,503 A | 6/1995 | Kusunose | |
| 5,751,475 A | 5/1998 | Ishiwata et al. | |
| 7,151,632 B2 | 12/2006 | Biss et al. | |
| 7,365,858 B2 | 4/2008 | Fang-Yen et al. | |
| 7,433,046 B2 * | 10/2008 | Everett et al. | 356/479 |
| 7,548,320 B2 * | 6/2009 | Chan et al. | 356/497 |
| 7,812,959 B1 | 10/2010 | Kim | |
| 8,184,298 B2 | 5/2012 | Popescu et al. | |
| 2003/0219809 A1 * | 11/2003 | Chen et al. | 435/6 |
| 2005/0099682 A1 | 5/2005 | Lauer | |
| 2005/0168808 A1 | 8/2005 | Ishiwata | |
| 2006/0291712 A1 | 12/2006 | Popescu et al. | |
| 2007/0242133 A1 | 10/2007 | Ooki | |
| 2009/0168158 A1 | 7/2009 | Schwertner et al. | |
| 2009/0290156 A1 | 11/2009 | Popescu et al. | |
| 2010/0094135 A1 | 4/2010 | Fang-Yen et al. | |

OTHER PUBLICATIONS

Haldar et al., "Deconvolved Spatial Light Interference Microscopy for Live Cell Imaging", IEEE Transactions on Biomedical Engineering, vol. 58, Issue 9, Sep. 2011.

Haldar et al., "Label-Free High-Resolution Imaging of Live Cells With Deconvolved Spatial Light Interference Microscopy", Conference Proceedings IEEE Engineering in Medicine and Biology Society, pp. 3382-3385, 2010.

Maruer et al., "Refining Common Path Interferometry with Spiral Phase Fourier Filter", Journal of Optics A: Pure and Applied Optics, 11 094023, pp. 1-7, 2009.

Maven Biotechnologies, White Paper on Label Free Internal Reflection Ellipsometry, pp. 1-8, downloaded Mar. 20, 2012, available at http://www.mavenbiotech.com/whitepaper.htm.

Przibilla et al., "Investigations on Label-Free Identification of Subcellular Tumor Cell Structures by Digital Holographic Phase Contrast Microscopy" DGaO-Proceedings, 2009.

Rodrigo et al., "Accurate Quantitative Phase Imaging Using Generalized Phase Contrast", Optics Express, vol. 16, No. 4, Feb. 18, 2008.

Waller et al., "Phase From Chromatic Aberrations", Optics Express, vol. 18, No. 22, Oct. 25, 2010.

Wang et al., "Label-Free Intracellular Transport Measured by Spatial Light Interference Microscopy", Journal of Biomedical Optics, vol. 16, Issue 2, Feb. 2011.

Yamauchi et al., "Label-Free Classification of Cell Types by Imaging of Cell Membrane Fluctuations Using Low-Coherent Full-Field Quantitative Phase Microscopy", Proceedings of SPIE-New Developments in Microscopy, vol. 7500, 2010, San Francisco, California, USA.

Popescu, Gabriel et al., "Imaging redbloodcell dynamics by quantitative phase microscopy". Blood Cells, Molecules, and Diseases 41, Apr. 1, 2008, pp. 10-16.

Search Report and Written Opinion from related PCT Application No. PCT/SE2012/051445 dated Jul. 3, 2013.

Search Report and Written Opinion from corresponding PCT Application No. PCT/SE2013/051257 dated Mar. 18, 2014.

* cited by examiner

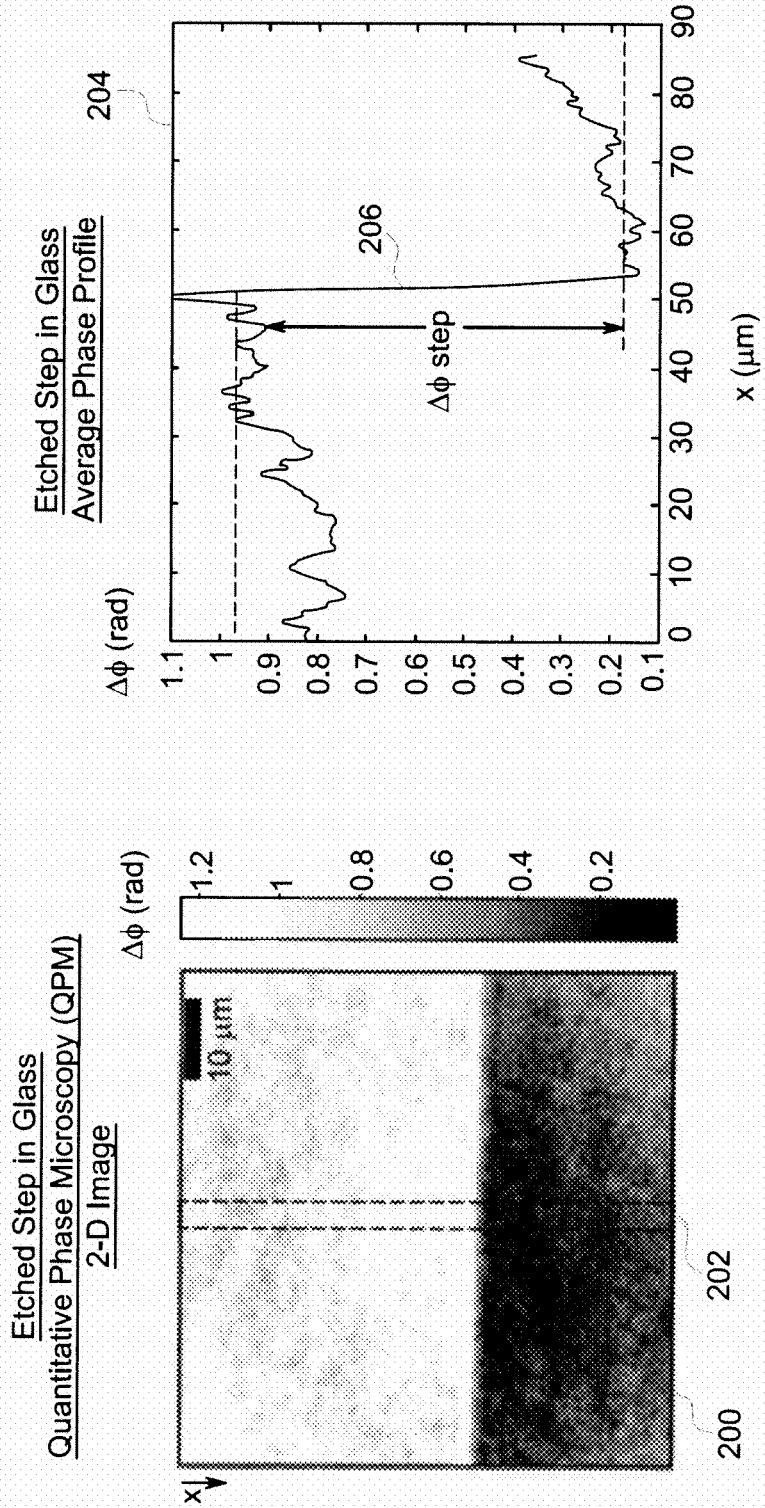

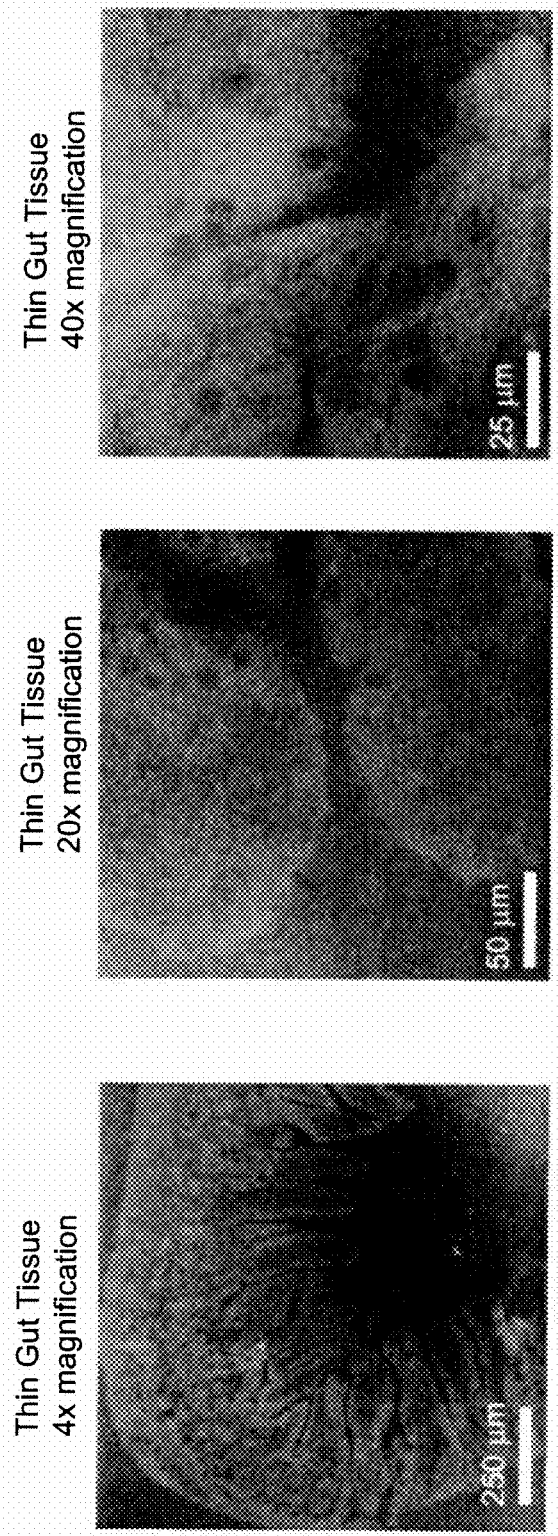

QUANTITATIVE PHASE MICROSCOPY FOR LABEL-FREE HIGH-CONTRAST CELL IMAGING

CROSS REFERENCE TO RELATED APPLICATIONS

This application is a continuation-in-part of U.S. patent application Ser. No. 13/335,748, filed on Dec. 22, 2011, which is herein incorporated by reference in its entirety.

FIELD

The embodiments relate generally to phase contrast microscopy. More specifically, some embodiments relate to quantitative phase microscopy for high-contrast cell imaging. Other aspects of the invention include a novel time multiplexing method to permit real-time image acquisition of the spatial variations of quantitative phase microscopy.

BACKGROUND

The identification of borders of cell bodies and/or cell nuclei in a microscopy image of a sample may be referred to as segmentation of cell bodes and/or nuclei in the image. To image structures of cells in a sample (e.g., for segmentation), staining or labeling techniques are often used to enhance contrast between different types of cell structures. For example, a specimen may be stained with dyes that react with DNA or RNA (e.g., ethidium bromide), or dyes that interact differently with the nucleus and the cytoplasm of a cell (e.g., hematoxylin-eosin). As another example, labels, which may be one or more colored agents (chromopores) and/or or one or more fluorescent agents (fluorophores), are useful in identifying a desired substance in a cell structure based on the presence of a specific tag. Such staining and labeling techniques aid in the identification of cell structures; however, staining or labeling using external contrast agents may affect the structure or other properties of interest of the sample being imaged. Further, in general, such staining or labeling cannot be performed on live cells.

Conventional phase-contrast imaging techniques (e.g., Zernike, different interference contrast (DIC)) enable imaging of cell monolayers with improved contrast as compared with bright-field imaging. These phase-contrast techniques, which do not require staining or labeling, generally can provide sufficient image contrast, but at the expense of additional optical components, light sources and alignment procedures.

Conventional phase imaging can be approximated as processing a series of traditional transmitted light images (e.g., by subtraction of in and out of focus images). While providing an image with enhanced edge features, the contrast is often not sufficient to ensure reliable automated segmentation of cells and/or nuclei.

Further, neither conventional optical imaging with labels and stains, nor conventional phase-contrast imaging provides quantitative thickness information regarding cell monolayers.

SUMMARY

Exemplary embodiments relate to methods and systems for producing quantitative phase images of samples. Some embodiments may be employed for producing high contrast quantitative phase images of biological samples. The produced high contrast quantitative phase images of biological samples may have sufficient contrast for label-free automated segmentation of cell bodies and/or nuclei in the image. The quantitative phase images may also provide information regarding sample thicknesses at various locations. The spatially resolved thickness information may provide sufficient information about cell conditions so as to make image segmentation unnecessary.

An exemplary embodiment is a system for tunable phase-contrast imaging. The system includes a light source for illuminating a sample with a main beam of light. In some embodiments the light source produces a beam of light with low coherence. The light may have a coherence length of less than 10 microns.

The system further includes at least one main beam optical element in a path of the main beam after the sample, which is configured to collect light diffracted by the sample and to collect light not diffracted by the sample. In some embodiments, the at least one main beam optical element includes a microscope objective and/or a tube lens.

The system also includes a beam splitter configured to split the light collected by the at least one main beam optical element into a first beam and a second beam. The first beam includes a first diffracted beam and a first undiffracted beam, and the second beam includes a second diffracted beam and a second undiffracted beam.

Along a path of the first beam, the system includes a first optical element (e.g., a lens) configured to focus the first undiffracted beam at a focal plane. The system also includes a mask at or near the focal plane configured to block at least a portion of the first diffracted beam and to transmit at least a portion of the focused first undiffracted beam. In some embodiments, the mask defines an aperture configured to transmit at least a portion of the focused first undiffracted beam. The mask may be configured to block most of the first diffracted beam and to transmit most of the focused first undiffracted beam. Generally, the mask filters modulation components from the undiffracted beam, which provides a clean phase reference.

A second optical element (e.g., a lens) is also in the path of the first beam after the mask. In some embodiments, the second optical element is configured to collimate the first undiffracted beam. The second optical element may have a same focal length as a focal length of the first optical element. The system may include a spatial filter including the first lens, the mask, and the second lens.

The system includes a movable mirror in the path of the first beam after the second optical element. In some embodiments, the system also includes a piezoelectric element to position the moveable mirror. The moveable mirror is configured to be positioned to produce each of a plurality of selected phase-shifts in the first beam relative to the second beam. In some embodiments, the plurality of selected relative phase shifts includes zero, $\pi/2$, and $\pi$. The plurality of selected relative phase shifts may further include $3\pi/2$.

The system also includes a second beam splitter in the path of the first beam and in a path of the second beam. The second beam splitter is configured to combine the first beam from the moveable mirror with the second beam for imaging by a two-dimensional (2-D) imaging system. In some embodiments, the second beam splitter is configured to combine the transmitted portion of the first undiffracted beam from the movable mirror and the second diffracted beam.

In some embodiments, an optical path length of the first undiffracted beam from the first beam splitter to the 2-D imaging system is about equal to an optical path length of the second diffracted beam from the first beam splitter to the 2-D imaging system.

In some embodiments, the system includes a third optical element (e.g., a lens) and a fourth optical element (e.g., a lens) in a path of the second beam. The third optical element may have a focal length about equal to a focal length of the fourth optical element. The fourth optical element may be configured to focus the second diffracted beam at the 2-D imaging system.

In some embodiments, the system further includes a computing device programmed to determine a quantitative phase image. The determination of the quantitative phase image may be based, at least in part, on measured 2-D phase-contrast images obtained with the movable mirror positioned for a relative phase shift of zero, positioned for a relative phase shift of $\pi/2$, and positioned for a relative phase shift of $\pi$. In some embodiments, the quantitative phase image is further based, at least in part, on a measured 2-D phase-contrast image obtained with the moveable mirror positioned for a relative phase shift of $3\pi/2$. The quantitative phase image may include quantitative information regarding a relative phase delay for each location in the quantitative phase image.

In some embodiments, the system is configured for label-free, high-contrast imaging of samples including one or more cells. The computing device may be further programmed to perform label-free segmentation of samples including cells and/or nuclei based on the quantitative phase image. The computing device may be further programmed generate quantitative thickness information for a cell monolayer sample based on at least a portion of the quantitative phase image.

Another embodiment is a method for quantitative phase imaging. The method includes directing a main beam of light through a sample, and collecting light diffracted by the sample and light not diffracted by the sample.

The method also includes splitting the collected diffracted and undiffracted light into a first beam including a first diffracted beam and a first undiffracted beam, and a second beam including a second diffracted beam and a second undiffracted beam. In some embodiments a beam splitter may be used to split the collected diffracted and undiffracted light.

The method also includes focusing the first undiffracted beam at a focal plane. At least a portion of the first diffracted beam is blocked at or near the focal plane, and at least a portion of the focused first undiffracted beam is transmitted at or near the focal plane. In some embodiments, blocking at least a portion of the first diffracted beam and transmitting at least a portion of the focused first undiffracted beam includes blocking a majority of the first diffracted beam. In some embodiments, a spatial filter positioned at or near the focal plane transmits at least a portion of the focused first undiffracted beam and blocks at least a portion of the first diffracted beam.

The method further includes directing the transmitted first undiffracted beam portion to a relative phase shift element. In some embodiments, the relative phase shift element is a moveable mirror. The relative phase may be adjusted using a piezoelectric element coupled with the moveable mirror.

The method also includes combining the first beam from the relative phase shift element with the second beam to obtain a combined beam, and directing the combined beam to a two-dimensional imaging device to produce phase-contrast images.

The method further includes adjusting the relative phase shift element to obtain a phase-contrast image corresponding to about zero relative phase shift between the first beam and the second beam. The method also includes adjusting the relative phase shift element to obtain a phase-contrast image corresponding to a relative phase shift of about $\pi/2$ between the phase-shifted first beam and the second beam. The method includes adjusting the relative phase shift element to obtain a phase-contrast image corresponding to a relative phase shift of about it between the phase-shifted first beam and the second beam.

The method includes producing a quantitative phase image based, at least in part, on the at least one phase-contrast image corresponding to about zero relative shift, on the at least one phase-contrast image corresponding to about $\pi/2$ relative shift, and on the at least one phase-contrast image corresponding to about $\pi$ relative shift using a computing device. The quantitative phase image may include quantitative information regarding a relative phase delay for each location in the quantitative phase image. In some embodiments, the method further comprises displaying the quantitative phase image.

In some embodiments, the method further comprises adjusting the relative phase shift element to obtain a phase-contrast image corresponding to a relative phase shift of about $3\pi/2$ between the phase-shifted first beam and the second beam. The quantitative phase contrast image may also be based, at least in part, on the at least one phase-contrast image corresponding to a relative shift of about $3\pi/2$.

In some embodiments, the method further includes displaying the quantitative phase image. The method may also include generating quantitative thickness information for each location in at least a portion of the quantitative phase image based on at least a portion of the quantitative phase image.

In some embodiments, the sample includes one or more cells and the quantitative phase image is a label-free, high-contrast image of the sample. In some embodiments, the sample includes a cell monolayer and the method further includes generating quantitative thickness information regarding the cell monolayer based on at least a portion of the quantitative phase image of the sample. In some embodiments, the method also includes performing label-free automated segmentation of cells and/or nuclei based on the quantitative phase image.

In certain embodiments described herein below in greater detail, a quantitative phase microscopy system is provided that is configured to sequentially capture images at a plurality (e.g., four) phase delays through the use of a novel time multiplexing method. Such systems permit real-time image acquisition in the spatial variations of the quantitative phase microscopy system.

In some embodiments as outlined below, a time multiplexing method is used in a quantitative phase microscopy system that permits real-time image acquisition in the spatial variations of the quantitative phase microscopy system. Real-time acquisition of QPM via time multiplexing method will allow monitoring dynamic biological processes, such as cardiac cell contraction and nervous system models stretching.

In a further embodiment of the invention, systems for phase contrast imaging are provided wherein the system is configured to apply a novel algorithm to the image data, thereby suppressing background "noise" and therefore improving the image quality by achieving a "speckle-free" background. The specific details of the algorithm and the resultant improved images are described below and also presented in FIGS. 25 and 26.

BRIEF DESCRIPTION OF DRAWINGS

Features and aspects of embodiments are described below with reference to the accompanying drawings, in which elements are not necessarily depicted to scale.

FIG. 6 is a two-dimensional image of quantitative phase microscopy data of glass with an etched step obtained using an example system and method.

FIG. 7 is a plot of the average phase profile for data falling within the broken lines in FIG. 5.

FIG. 18 is a two-dimensional image of a second set of quantitative phase microscopy data of a thin gut tissue section sample obtained using the example system and method with a microscope configured for 4× magnification.

FIG. 19 is a two-dimensional image of a third set of quantitative phase microscopy data of the thin gut tissue section sample produced from phase-contrast images obtained with the microscope configured for 20× magnification.

FIG. 20 is a two-dimensional image of a fourth set of quantitative phase microscopy data of the thin gut tissue section sample obtained with the microscope objective configured for 40× magnification.

DETAILED DESCRIPTION

Some embodiments are described herein relative to a system and method for quantitative phase imaging. Example embodiments generate multiple phase-contrast images with various relative phase shifts between light diffracted by a sample and light not diffracted by the sample to obtain a quantitative phase image that is relatively free from artifacts. Some embodiments provide phase-contrast microscopy systems and methods that provide quantitative optical thickness information regarding thin biological samples (e.g., cell monolayers). Some embodiments may provide sufficient image contrast to perform label-free automated segmentation of cell bodies and/or nuclei.

Figure 1:
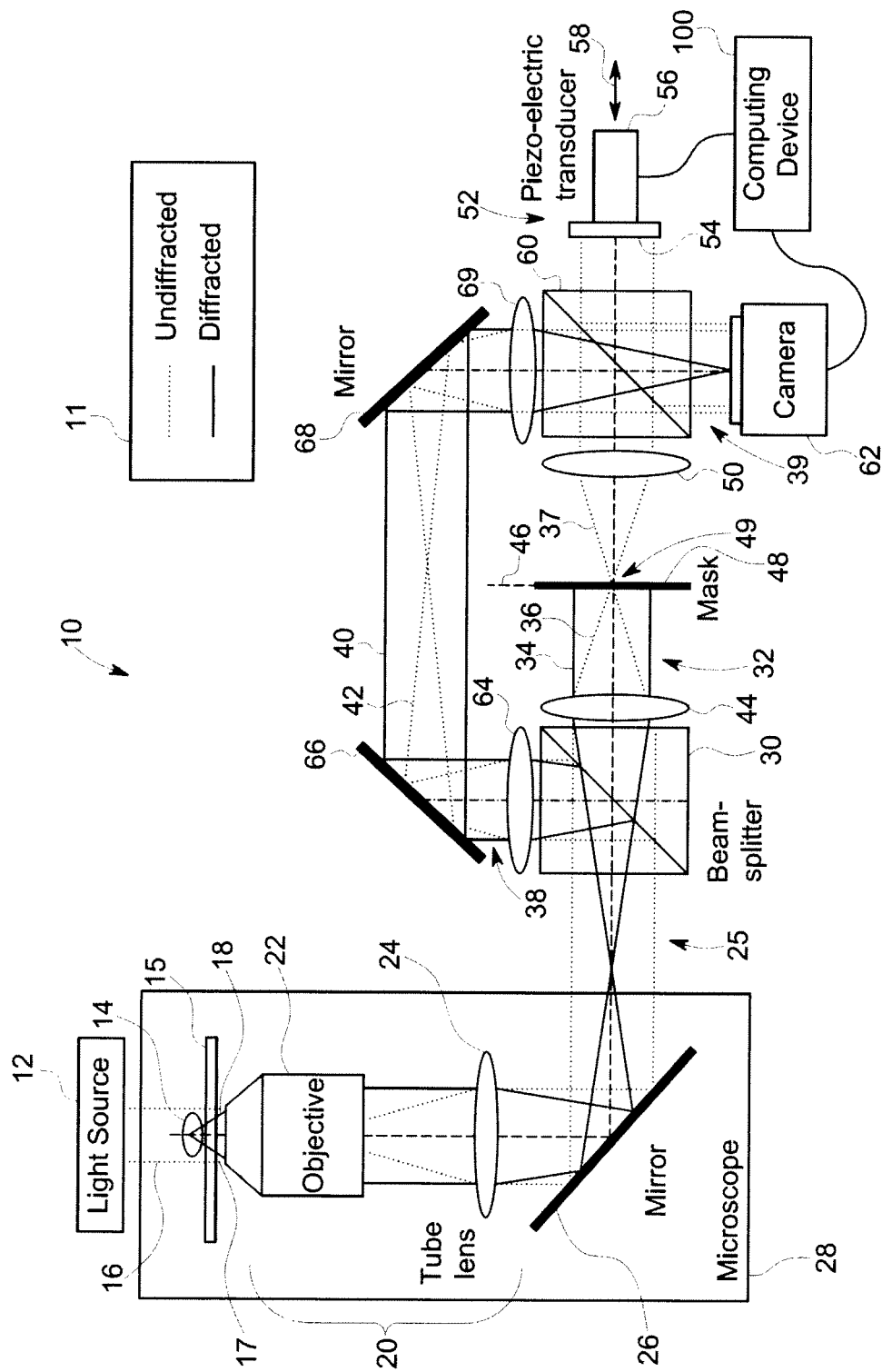
FIG. 1 schematically depicts an exemplary system for phase-contrast imaging, in accordance with some embodiments.

FIG. 1 schematically depicts an exemplary system 10 for performing quantitative phase-contrast (PC) imaging, in accordance with some embodiments. The system 10 includes a light source 12 for illuminating a sample 14 with a main beam of light 16. In some embodiments, various optical elements, such as lenses and filters, may be included in the light source 12 or positioned between the light source 12 and the sample 14. The light source 12 may be a low temporal coherence light source. For example, in some embodiments the light source may produce a main beam with a coherence length of less than about 2.5 microns.

The sample 14 may be a translucent or transparent sample. In some embodiments, the sample may be a dry sample (e.g., on a coverslip) or a wet sample (e.g., live cells in a chamber). In some embodiments, the sample may be in a micro titer plate or in a t225 flask. In some embodiments, the sample may be between 2 microns and 10 microns thick depending on wavelength of light used The main beam of light 16 interacts with the sample 14 resulting in light that is diffracted by the sample (diffracted light) 18 and light that is not diffracted by the sample (undiffracted light) 17. The diffracted light 18 and the undiffracted light 17 are collected by at least one main beam optical element 20, in the path of the main beam 16 after the sample 14. As indicated by the legend 11, in the present diagram, light diffracted by the sample is depicted with solid lines, and light that is not diffracted by the sample is depicted with broken lines. In some embodiments, the at least one main beam optical element 20 may include an objective 22, a tube lens 24, or both, as shown. As illustrated, one or more transparent or translucent optical elements 15 (e.g., a glass slide, a coverslip, a chamber window, etc.) may separate the at least one main beam optical element 20 from the sample 14.

In some embodiments, the at least one main beam optical element 20 for collecting light may be a portion of a microscope 28 (e.g., the microscope objective 22 and the tube lens 24). In some embodiments, the light source 12 may be part of the microscope 28, may be separate from the microscope 28, or may be partially incorporated into the microscope 28. The microscope 28 may further include one or more mirrors (e.g., mirror 26) for directed the diffracted light 18 and the undiffracted light 17. The microscope may be connected to and/or in communication with a computing device 100. The computing device 100 is described in more detail below with respect to FIG. 5.

In the system 10, the collected light (diffracted light 18 and undiffracted light 17) are split into two separate paths, a first light beam 32 directed along a first path and a second light beam 38 directed along a second path. The light beams 32, 38 are optically manipulated along one or both of the paths before being combined and directed to an imaging device 62, where interference between the first beam portion of the combined beam 39 and the second beam portion of the combined beam 39 produces a phase-contrast image.

The collected light 25, including the diffracted light 18 and undiffracted light 17, is split by a first beam splitter 30 into a first beam 32 including a first diffracted beam 34 and a first undiffracted beam 36, and a second beam 38, including a second diffracted beam 40 and a second undiffracted beam 42. As shown, the collected light 25 may be split by a cube beam splitter 30. In other embodiments, other optical elements for splitting light may be used (e.g., a plate beam splitter).

Along the first path, at least a portion of the first diffracted beam 34 is blocked and at least a portion of the first undiffracted beam 36 is transmitted. The system 10 includes a first optical element (e.g., lens 44) in a path of the first beam 32 that focuses the first beam 32 at a focal plane 46. The system 10 also includes a mask 48 positioned at or near the focal plane 46. The mask 46 is configured to block at least a portion of the first diffracted beam 34 and transmit at least a portion of the first undiffracted beam 36. For example, the mask 46 may comprise a material that blocks light and the mask 46 may define aperture 49 positioned at or near the location of the focused first undiffracted beam 26. Because the first diffracted beam 34 is not focused at the focal plane 46, most of the first diffracted beam 34 will not pass through the aperture 49 and will be blocked by the mask. Because the first undiffracted beam 36 is focused at the focal plane 46, most, or all, of the first diffracted beam will pass through the aperture 49. In some embodiments, the mask 46 may be described as a spatial filter.

After the mask 48, the transmitted portion of the first undiffracted beam 37 encounters a moveable mirror 54 and may be shifted relative to the second beam 38. The system may include second optical element (e.g., lens 50) after the mask 48 and before the moveable mirror 54. In some embodiments, the second optical element (e.g., lens 50) may be configured to collimate the transmitted undiffracted beam portion 37. In some embodiments, the second optical element (e.g., lens 50) may have a focal length that is about equal to a focal length of the first optical element (e.g., lens 44).

As noted above, the system 10 further includes a moveable mirror 54 in the path of the first beam 32, which includes the transmitted undiffracted beam portion 37, after the second optical element (e.g., lens 50). The moveable mirror 54 is configured to be positioned to produce each of a plurality of selected phase shifts in the first beam 32 relative to the second beam 38. The selected relative phase shifts may include any of zero, $\pi/2$, $\pi$, and $3\pi/2$. The amount that the moveable mirror 54 must be moved to produce the required phase shifts depends on the main wavelength of light illuminating the sample. For example, if there is no relative phase shift with the moveable mirror 54 at an initial position, and the main wavelength of main beam of illuminating light 16 is $\lambda$, the relationship between the displacement of the mirror from the initial position ($\Delta P$) and the relative phase shift ($\Delta\theta$) is given below.

$$\Delta P = \frac{\Delta\theta}{4\pi}\lambda \quad (1)$$

For light with a wavelength of 840 nm, a $\pi/2$ relative phase shift corresponds to a 105 nm displacement of the moveable mirror 54. The moveable mirror 54 may be part of a moveable mirror unit 52 that includes additional portions or components for precisely displacing the moveable mirror 54. For example, in system 10, the moveable mirror unit 52 also includes a piezoelectric transducer 56 that translates the mirror along the beam path as indicated by arrow 58. An input voltage to the piezoelectric transducer 56 determines how far the movable mirror 54 is displaced, which is proportional to relative phase shift. In some embodiments, the piezoelectric transducer 56 may be controlled using the computing device 100, (see description of FIG. 5 below).

In other embodiments, other devices, systems or mechanisms may be used to displace the moveable mirror 54. For example, the moveable mirror may be translated by any one or any combination of the following: a piezoelectric actuator, a linear variable differential transformer (LVDT) driven stage, a precision screw driven stage, a voice coil actuator, etc.

After the first beam 32, which includes the potentially phase-shifted transmitted portion of the first undiffracted beam 37, reflects off of the moveable mirror, it is directed by a second beam splitter 60 into a two-dimensional imaging device (e.g., camera 62).

Turning to the path of the second beam 38, the second beam 38 includes a second diffracted beam 40 and a second undiffracted beam 42. A path length of the first undiffracted beam 36, as measured from the first beam splitter 30 to the camera 62, may be about equal to a path length of the second diffracted beam 40, as measured from the first beam splitter 30 to the camera 62. The second beam 38 may encounter a third optical element (e.g., lens 64), which focuses the second undiffracted beam 42. In some embodiments, a focal length of the third optical element (e.g., lens 64) may be about equal to a focal length of the first optical element (e.g., lens 44). The second beam 38 may be directed along its path by one or more mirrors (e.g., mirrors 66, 68). The second beam 38 may also encounter a fourth optical element (e.g., lens 70) before it is combined with the first beam 32 at the second beam splitter 60. In some embodiments, the fourth optical element (e.g., lens 70) may have a focal length about equal to a focal length of the third optical element (e.g., lens 50). In some embodiments, the fourth optical element (e.g., lens 70) may focus the second diffracted beam at the 2-D imaging device (e.g., camera 62).

In some embodiments, the path of the second beam may include a second mask (not shown), which is configured to block at least a portion of the second undiffracted beam 42 and configured to transmit at least a portion of the second diffracted beam 40. In such an embodiment, the second mask may take the form of an element that transmits most incident light but blocks most light in a region that is a focal point of the second undiffracted beam 42. Although blocking at least some of the second undiffracted beam 42 may increase contrast in the phase-contrast image, image quality in a center of the phase-image may be reduced due to blocking the portion of the diffracted beam 40 incident on the second mask at the focal point of the second undiffracted beam 42.

The second beam splitter 60 combines the first beam 32, which includes the possibly phase-shifted, transmitted, first undiffracted beam portion 37, with the second beam 38, which includes the second diffracted beam 40 and may include the second undiffracted beam 42. Interference between the transmitted, first undiffracted beam portion 37 and the second diffracted beam 40 produces a phase-contrast (PC) image at the 2-D imaging device (e.g., camera 62).

The 2-D imaging device may be any 2-D imaging device with suitable resolution, (e.g., a charge coupled device (CCD) camera, a photomultiplier tube (PMT) camera, a high resolution video camera, or other imaging device suitable resolution). In some embodiments, the 2-D imaging device (e.g., camera 62) may be configured to provide the images or image data to the computing device 100 for analysis. As used herein, the term "image" may refer to one or both of a displayed image, and data or information corresponding to an image. Thus, obtaining an image may refer to obtaining an analog image or obtaining data corresponding to a digital image. Further, data corresponding to an image may be raw image data, processed image data (e.g., filtered, smoothed, cropped), compressed image data, etc. Further, the image data may be stored or transmitted in a variety of formats (e.g., JPG, bitmap, postscript, etc.), as would be appreciated by one of skill in the art.

Figure 2:
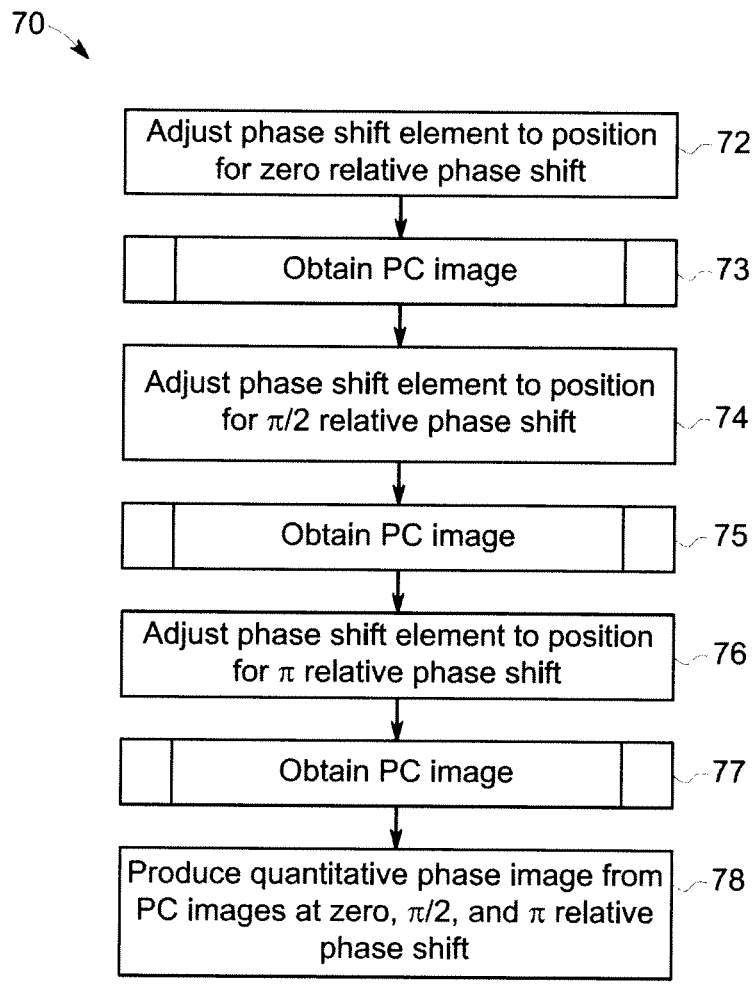
FIG. 2 is a flow chart depicting an exemplary method for quantitative phase imaging including obtaining phase-contrast images for zero, π/2, and π relative phase shifts, in accordance with some embodiments.
Figure 3:
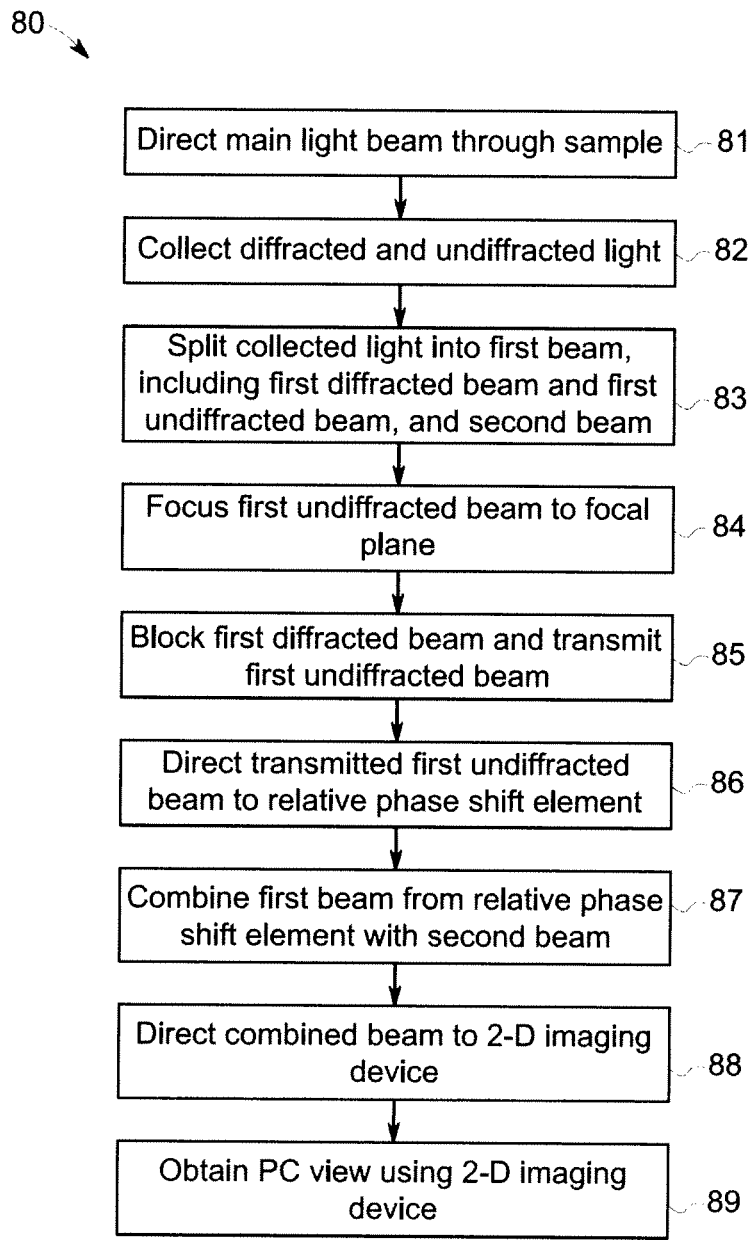
FIG. 3 is a flow chart depicting the "obtain phase-contrast image" portion of the method depicted in FIG. 2.
Figure 4:
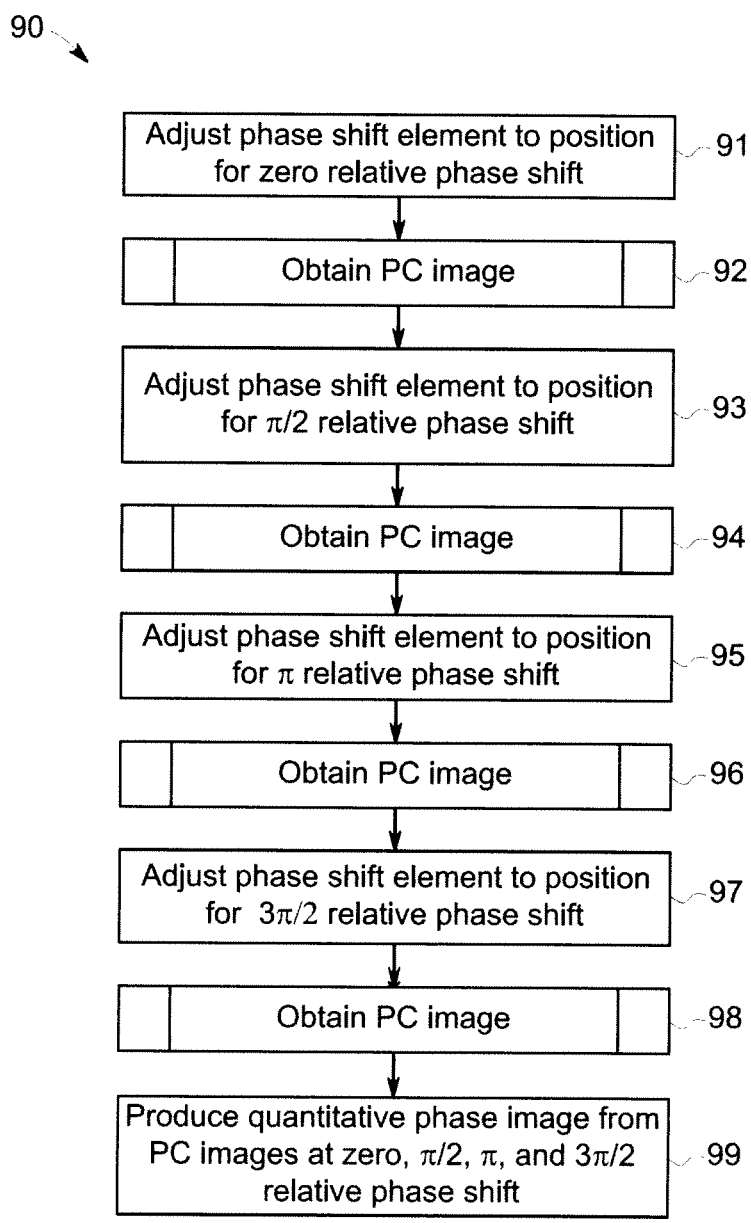
FIG. 4 is a flow chart depicting another exemplary method for quantitative imaging that includes obtaining phase-contrast images for zero, π/2, π, and 3π/2 relative phase shifts, in accordance with some embodiments.

FIGS. 2-4 are flow charts schematically illustrating exemplary methods for generating a quantitative phase image of a sample. For illustrative purposes, the methods 70, 80 and 90 are described with respect to system 10 depicted in FIG. 1. However, other systems with other configurations may be used to perform methods 70, 80 and 90, as would be appreciated by one of skill in the art.

FIG. 2 illustrates an exemplary method 70 for producing a quantitative phase image based on three different relative phase shifts between the first beam and the second beam. In some embodiments, the method for quantitative phase imaging may include obtaining phase contrast images with the phase shift element positioned at phase shifts of zero, π/2, and π as schematically depicted in the flow chart of FIG. 2. The first step of method 70, step 72, is adjusting a phase shift element to a position for zero relative phase shift between the first beam 32 and the second beam 34. Generally, step 72 may be accomplished by performing a method 80 for obtaining a phase-contrast view of a sample, and observing the resulting sample view while adjusting the phase shift element until the view indicates a position for zero relative phase shift between the first beam 32 and the second beam 34 is reached.

FIG. 3 schematically depicts the method 80 for obtaining a phase-contrast view of a sample in a flow diagram. A main light beam 14 is directed through a sample 14 (step 81). The main light beam 14 may be from a light source 12. The main light beam may have low temporal coherence. For example, in some embodiments, the main light beam may have a coherence length of less than about 10 microns.

Light diffracted by the sample 18 and undiffracted light 17 are collected (step 82). As illustrated in FIG. 1, the diffracted 18 and undiffracted light 17 may be collecting using one or more main beam optical elements (e.g., objective 22 and tube lens 24), which, in turn, may be components of a microscope 28.

The collected light 25 is split into a first beam 32 including a first diffracted beam 34 and a first undiffracted beam 36, and a second beam including a second diffracted beam 40 and a second undiffracted beam 42 (step 84). As shown, the collected light 25 may be split by a cube beam splitter 30.

The first undiffracted beam 36 is focused to a focal plane 46 (step 84). As shown, the first undiffracted beam 36 may be focused by a first optical element (e.g., first lens 44). In other embodiments, multiple lenses or one or more other types of optical elements (e.g., curved mirrors) may used to focus the first undiffracted beam 36.

At or near the focal plane 46, at least a portion of the first diffracted beam 34 is blocked and at least a portion of the first undiffracted beam 36 is transmitted (step 85). A mask 48 or a spatial filter at or near the focal plane 46 may be used to block at least a portion of the first diffracted beam 34 and to transmit at least a portion of the first undiffracted beam 36. For example, the mask may include a transmissive portion or aperture 49 positioned to allow at least a portion of, most of, or substantially all of the focused first undiffracted beam 36 past the mask. Away from the transmissive portion or aperture 49, the mask 48 may be configured to block at least a portion of, a most of, or substantially all of the first diffracted beam 34, which is not focused at the focal plane 46.

In some embodiments, the transmitted first undiffracted beam portion 37 may pass through a second optical element (e.g., lens 50). The second optical element may be configured to collimate the transmitted first undiffracted beam portion 37. The transmitted first undiffracted beam portion 37 is directed to a relative phase shift element (step 86). The relative phase shift element may be an element that lengthens the path of the first beam 32 relative to the second beam 38. As shown, the relative phase shift element may be a moveable mirror 54, which may be part of a moveable mirror unit 52 that includes a mechanism for translating the moveable mirror (e.g., piezo-electric transducer 56). In other embodiments, the relative phase shift element may change an optical path length of the first beam with respect to the second beam without changing a physical path length. For example, in some embodiments, various optical elements having an index of refraction different than that of air and various lengths may be inserted into the path of the first beam to obtain the phase shifts. As another example, in some embodiments, various optical elements of the same length with different refractive indices may be inserted into the path of the first beam to obtain the phase shifts. After the first beam 32 encounters the relative phase shift element, the first beam 32, which includes the transmitted first undiffracted portion 37, is combined with the second beam 38, which includes the second diffracted beam portion 40 (step 87). As illustrated in FIG. 1, the first beam 32 and the second beam 38 may be combined with a second beam splitter 60. In some embodiments, the second beam 38 may encounter one or more additional optical elements (e.g., lens 64 and lens 69) before being combined with the first beam 32.

The combined beam 39 is directed to a 2-D imaging device (e.g., camera 62) (step 88). For example, in system 100, the second beam splitter 60 is used to direct the first beam portion of the combined beam 62 to the camera 62, and the mirror 68 is used to direct the second beam portion of the combined beam 39 to the camera 62. As shown in FIG. 1, an optical element such as lens 69 may be used to focus the second diffracted beam portion of the combined beam 39 onto the camera 62.

Adjusting the phase shift element to a position for zero relative phase shift, according to step 72 of FIG. 2, may involve actively observing a current phase-contrast view from the camera 62 as a position of the phase shift element (e.g., moveable mirror 54) is adjusted. When the phase shift element is at a position of zero relative phase shift between the first beam 32 and the second beam 38, the phase-contrast view will have a relatively high contrast (e.g., a maximum contrast) as compared to when the phase shift element is away from a position of zero relative phase shift.

After the phase shift element is positioned for zero relative phase shift (step 72), a phase-contrast image at zero phase shift is obtained (step 73). A phase-contrast image may be captured using the same 2-D imaging device used to observe the view in step 89 of FIG. 3. The camera 32 may capture a phase-contrast image and save it to internal memory or storage of the camera 32 and/or send the image to the computing device 100 for analysis and/or storage. Thus, a phase-contrast image at zero phase shift may be obtained from an imaging device or the memory of a device that received the image from the imaging device.

After the first image is obtained in step 73, the phase shift element is adjusted to a position corresponding to a phase shift of π/2 (step 74). As explained above, given a beam with a main wavelength λ, equation 1 above may be used to determine how far a moveable mirror should be displaced from the zero relative phase shift position (ΔP) to obtain a desired relative phase shift (Δθ). For example, as noted above, for light with a wavelength of 840 nm, a π/2 relative phase shift corresponds to a 105 nm displacement (ΔP) of the moveable mirror 54. Thus, the movable mirror 54 may be displaced by 105 nm to position for a phase shift of π/2. A phase-contrast image is obtained with the phase shift element positioned for π/2 relative phase shift (step 75). The phase contrast image may be obtained (step 75) using the method 80 illustrated in FIG. 2.

The phase shift element is then adjusted to a position to attain a phase shift of π/2 between the first beam 32 and the second beam 38 (step 76). For example, for light with a wavelength of 840 nm, a π relative phase shift corresponds to a 210 nm displacement of the moveable mirror 54 from the zero relative phase shift position. A phase-contrast image is obtained with the phase shift element positioned for π relative phase shift (step 77). As noted above, the phase contrast view may be obtained and captured (step 77) using the method 80 illustrated in FIG. 2. After the phase-contrast images corresponding to the phase shift element being positioned for zero, π/2 and π relative phase shifts have been obtained, a quantitative phase image is produced (step 78) from the phase-contrast images. Although the method 80 is described as obtaining the phase contrast views in the order of zero relative phase shift, π/2 relative phase shift and π relative phase shift, in practice, after the location for zero relative phase shift is determined, the phase-contrast images may be obtained in any order. Further, although the method 70 is described as obtaining a phase-contrast image at each of zero, π/2, and π relative phase shifts, multiple phase-contrast images could be obtained with the phase shift element at a given position and the multiple images combined (e.g., averaged) before being used to produce the quantitative phase image.

A phase contrast image may be represented as interference between diffracted and undiffracted light from a sample according to the following equation:

$$I_0(x,y) = I_U - I_D + 2\sqrt{I_U I_D}\cos(\Delta\phi(x,y)) \qquad (2)$$

where $I_0(x,y)$ is the phase contrast image intensity at each location, $I_U$ is the image intensity from the undiffracted light, $I_D$ is the image intensity from the diffracted light and $\Delta\phi(x,y)$ is the two-dimensional phase shift. Although $I_U(x,y)$ and $I_D(x,y)$ are both functions of location (x,y), they are merely represented by $I_U$ and $I_D$ in the equations for simplicity.

If the relative phase shift in the system between the first beam and the second beam is changed in a controlled manner and phase contrast images are obtained at relative phase shifts of zero, π/2, π, and 3π/2, the following equations apply:

$$I_1(x,y) = I_U - I_D + 2\sqrt{I_U I_D}\cos\left(\Delta\varphi(x,y) + \frac{\pi}{2}\right) \qquad (3)$$

$$I_2(x,y) = I_U - I_D + 2\sqrt{I_U I_D}\cos(\Delta\varphi(x,y) + \pi) \qquad (4)$$

$$I_3(x,y) = I_U - I_D + 2\sqrt{I_U I_D}\cos\left(\Delta\varphi(x,y) + \frac{3\pi}{2}\right) \qquad (5)$$

The equation $I_0$ for phase contrast at zero relative phase shift (2), the equation $I_1$ for phase contrast at π/2 relative phase shift (3), and the equation $I_2$ for phase contrast at π relative phase shift (4) may be combined to yield an equation for the quantitative phase across an image that depends on $I_0$, $I_1$, and $I_2$ as follows:

$$\Delta\varphi(x,y) = -\arctan\left(\frac{I_0 + I_1 - 2I_1}{I_2 - I_1}\right) \qquad (6)$$

Equation 6 may be used to determine the relative phase $\Delta\phi(x,y)$ at each location (x,y) to create a quantitative phase image, which includes quantitative phase information at each location, from phase contrast images $I_0$, $I_1$, and $I_2$ having relative phase shifts, zero, π/2 and π respectively. The resulting quantitative phase image may be referred to as a 3-step image.

FIG. 4 illustrates an exemplary method 90 for producing a quantitative phase image based on four phase shifts. In some embodiments, the method for quantitative phase imaging may include obtaining phase contrast images with the phase shift element positioned at phase shifts of zero, π/2, π, and 3π/2 as schematically depicted in the flow chart of FIG. 4. The method 90 includes steps 91-96 for adjusting the phase shift element for zero, π/2, and π relative phase shifts and obtaining a phase-contrast view at each relative phase shift, which parallels corresponding steps 72-77 of method 70. In method 90, the phase shift element is also adjusted to a position for 3π/2 relative phase shift (step 97) and a phase-contrast image is obtained at that phase shift (step 98). As noted above, method 80 of FIG. 3 may be used to obtain the desired phase-contrast view, which may be captured as an image. A quantitative phase image is produced from the phase contrast images at zero, π/2, π, and 3π/2 relative phase shifts.

If $I_0(x,y)$ is the phase-contrast image intensity at zero relative phase shift, $I_1(x,y)$ is the phase-contrast image intensity at π/2 relative phase shift, $I_2(x,y)$ is the phase-contrast image intensity at π relative phase shift, and $I_3(x,y)$ is the phase-contrast image intensity at 3π/2 relative phase shift, the quantitative phase $\Delta\phi(x,y)$ at each location in the image $\Delta\phi(x,y)$ can be obtained using equation 7 below, which is derived from equations 2-5 above.

$$\Delta\varphi(x,y) = -\arctan\left(\frac{I_3 - I_1}{I_2 - I_0}\right) \qquad (7)$$

The resulting quantitative phase image may be referred to as a 4-step image. Examples of 4-step quantitative phase images appear in FIGS. 6, 8-15, 17 and 18-23.

The quantitative phase image values Δφ(x,y) for method 70 may be calculated from the phase contrast images $I_0$, $I_1$, and $I_2$ by using a computing device (see discussion regarding FIG. 5 below) to evaluate equation 6 or an equivalent expression or approximation. For locations where $I_2$ is equal to $I_1$, the difference $(I_2-I_1)$ may be defined as a small non-zero value to avoid issues regarding a zero denominator in equation 6. Similarly, the quantitative phase data values Δφ(x,y) for method 90 may be calculated from the phase contrast images $I_0$, $I_1$, $I_2$, and $I_3$ by using a computing device to evaluate equation 7 or an equivalent expression or approximation. For locations where $I_2$ is equal to $I_0$, the difference $(I_2-I_0)$ may be defined as a small non-zero value to avoid issues regarding a zero denominator in equation 7.

In some embodiments, the calculation of a quantitative phase value would be performed for each location (e.g., for each pixel or for each data point $(x_o, y_o)$). In other embodiments, the phase-contrast image data may be processed (e.g., averaged across a number of pixels to reduce the effects of noise) before the quantitative phase data is calculated. One of ordinary skill in the art will appreciate that many different computer programs and algorithms may be used to produce the quantitative phase data from the phase-contrast image data.

In some embodiments, a method (e.g., method 70, method 90) may further include displaying a quantitative phase image on a visual display device 122 (see description of FIG. 5 below). Examples of 4-step quantitative phase images appear in FIGS. 6, 8-15, 17 and 18-23.

In some embodiments, a method (e.g., method 70, method 90) may further include calculating a thickness of at least a portion of a sample based on at least a portion of the quantitative phase image data. The calculation may be a thickness at each location in the quantitative phase image, a thickness at each location for at least a portion of the locations in the quantitative phase image, or may be a profile along the quantitative phase image, which may average multiple lines of pixels to obtain the profile. See description regarding FIG. 7 below.

Figure 5:
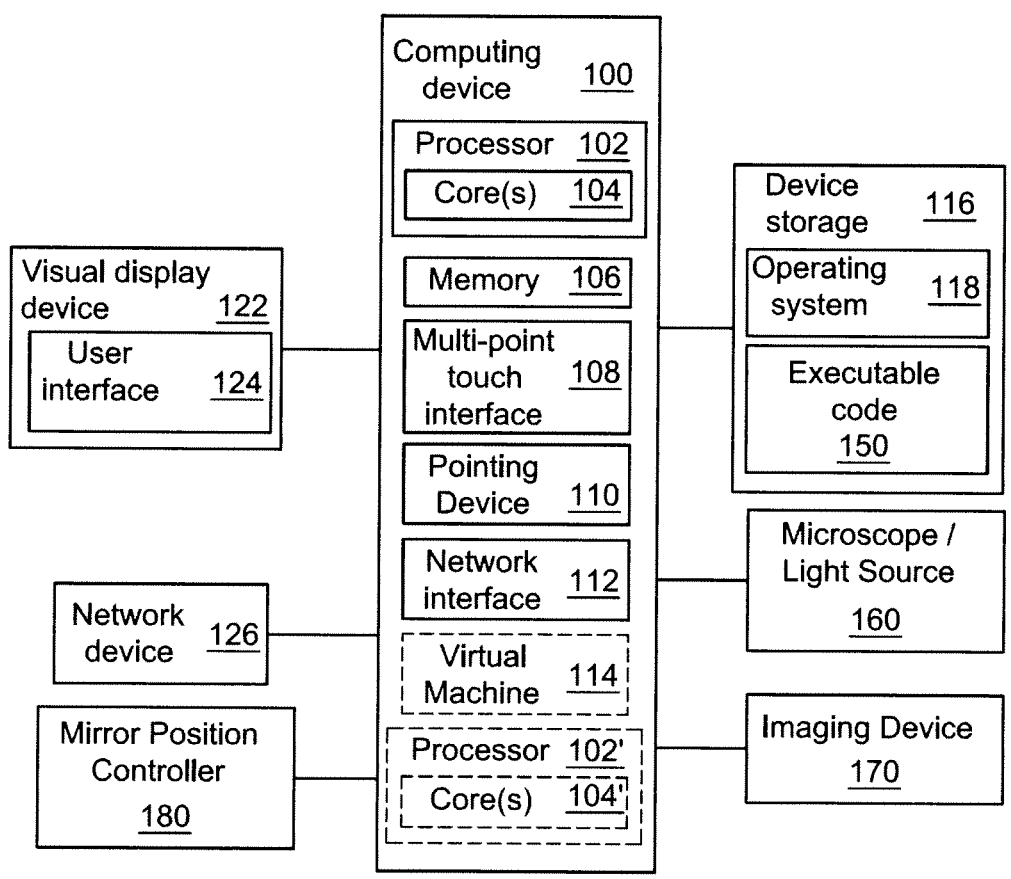
FIG. 5 illustrates an exemplary computing environment suitable for practicing exemplary embodiments taught herein.

FIG. 5 illustrates an exemplary computing environment suitable for practicing embodiments, including exemplary methods and systems taught herein. The environment includes a computing device 100 with associated peripheral devices. Computing device 100 is programmable to implement executable code 150 for performing various methods, or portions of methods, taught herein. Computing device 100 includes a storage device 116, such as a hard-drive, CD-ROM, or other non-transitory computer readable media. Storage device 116 may store an operating system 118 and other related software. Computing device 100 may further include memory 106. Memory 106 may comprise a computer system memory or random access memory, such as DRAM, SRAM, EDO RAM, etc. Memory 106 may comprise other types of memory as well, or combinations thereof. Computing device 100 may store, in storage device 116 and/or memory 106, instructions for implementing and processing each portion of the executable code 150.

The executable code 150 may include code for analyzing phase-contrast images to produce three-step and/or four-step quantitative phase images. In some embodiments, the executable code 150 may include image processing functionality (e.g., crop, smooth, filter, define region of interest, etc.) for processing phase-contrast images and/or quantitative phase images. The executable code 150 may include code for displaying the phase-contrast phase images and/or the quantitative phase images. In some embodiments, the executable code 150 may include code for determining thickness information corresponding to one or more locations in a quantitative phase image.

In some embodiments, the executable code 150 may further include code for performing automated segmentation of cell bodies and/or cell nuclei based on the quantitative phase image. One of ordinary skill in the art would understand that many known automated segmentation methods and techniques could be employed for automatic segmentation, which may include watershed feature detection, statistically driven thresholding, (e.g., Otsu, mean, MinError, Huang, triangles, and MinMax thresholding) and/or edge enhancing filters (e.g., unsharp masking, Sobel filtering, Gaussian filters, Kalman filters). In some embodiments, the executable code 150 may include functionality for user-assisted segmentation of cells and/or nuclei (e.g., tools allowing users to indicate cell boundaries or nuclei boundaries within a quantitative phase image). In other embodiments, segmentation may be performed entirely manually by a user.

Computing device 100 also includes processor 102, and may include one or more additional processor(s) 102', for executing software stored in the memory 106 and other programs for controlling system hardware, peripheral devices and/or peripheral hardware. Processor 102 and processor(s) 102' each can be a single core processor or multiple core (104 and 104') processor. Virtualization may be employed in computing device 100 so that infrastructure and resources in the computing device can be shared dynamically. Virtualized processors may also be used with executable code 150 and other software in storage device 116. A virtual machine 114 may be provided to handle a process running on multiple processors so that the process appears to be using only one computing resource rather than multiple. Multiple virtual machines can also be used with one processor.

A user may interact with computing device 100 through a visual display device 122, such as a computer monitor, which may display a user interface 124 or any other interface. The user interface 124 of the display device 122 may be used to display phase-contrast images, quantitative phase images, and/or user controls for controlling various peripheral devices. The visual display device 122 may also display other aspects or elements of exemplary embodiments (e.g., an icon for storage device 116). Computing device 100 may include other I/O devices such a keyboard or a multi-point touch interface (e.g., a touchscreen) 108 and a pointing device 110, (e.g., a mouse, trackball and/or trackpad) for receiving input from a user. The keyboard 108 and the pointing device 110 may be connected to the visual display device 122 and/or to the computing device 100 via a wired and/or a wireless connection. Computing device 100 may include other suitable conventional I/O peripherals.

In some embodiments, computing device 100 receives information (e.g., data or images) from, and/or sends information to, an imaging device 170 (e.g., camera 62 of FIG. 1) via a wired connection, via a wireless connection and/or via physical transfer of a storage device (e.g., a flash drive). In some embodiments, computer device 100 includes executable code for controlling one or more aspects of the imaging device 170 (e.g., an acquisition rate, an image resolution, etc.). In some embodiments, the imaging device 170 itself may include a user interface for controlling imaging parameters (e.g., an acquisition rate, an image resolution, etc.).

In some embodiments, the computing device 100 may receive information from and/or send information to a mirror position controller 180. For example, the computing device 100 may receive information regarding the position of the moveable mirror 54 and/or may direct the mirror position controller 180 to change a position of the moveable mirror 54. In some embodiments, the mirror position controller 180 may be integrated into the computing device 100.

In some embodiments, the computing device 100 may receive information from and/or send information to a microscope/light source 160. For example, parameters of the light source, such as brightness, may be observed and/or controlled using the computing device 100. As another example, for a microscope that is digitally controlled, parameters of the microscope (e.g., focus or filtering) may be observed and or controlled using the computing device 100.

Computing device 100 may include a network interface 112 to interface with a network device 126 via a Local Area Network (LAN), Wide Area Network (WAN) or the Internet through a variety of connections including, but not limited to, standard telephone lines, LAN or WAN links (e.g., 802.11, T1, T3, 56 kb, X.25), broadband connections (e.g., ISDN, Frame Relay, ATM), wireless connections, controller area network (CAN), or some combination of any or all of the above. The network interface 112 may comprise a built-in network adapter, network interface card, PCMCIA network card, card bus network adapter, wireless network adapter, USB network adapter, modem or any other device suitable for enabling computing device 100 to interface with any type of network capable of communication and performing the operations described herein.

Moreover, computing device 100 may be any computer system such as a workstation, desktop computer, server, laptop, handheld computer or other form of computing or telecommunications device that is capable of communication and that has sufficient processor power and memory capacity to perform the operations described herein.

Computing device 100 can be running any operating system 118 such as any of the versions of the MICROSOFT WINDOWS operating systems, the different releases of the Unix and Linux operating systems, any version of the MACOS for Macintosh computers, any embedded operating system, any real-time operating system, any open source operating system, any proprietary operating system, any operating systems for mobile computing devices, or any other operating system capable of running on the computing device and performing the operations described herein. The operating system may be running in native mode or emulated mode.

Figure 24:
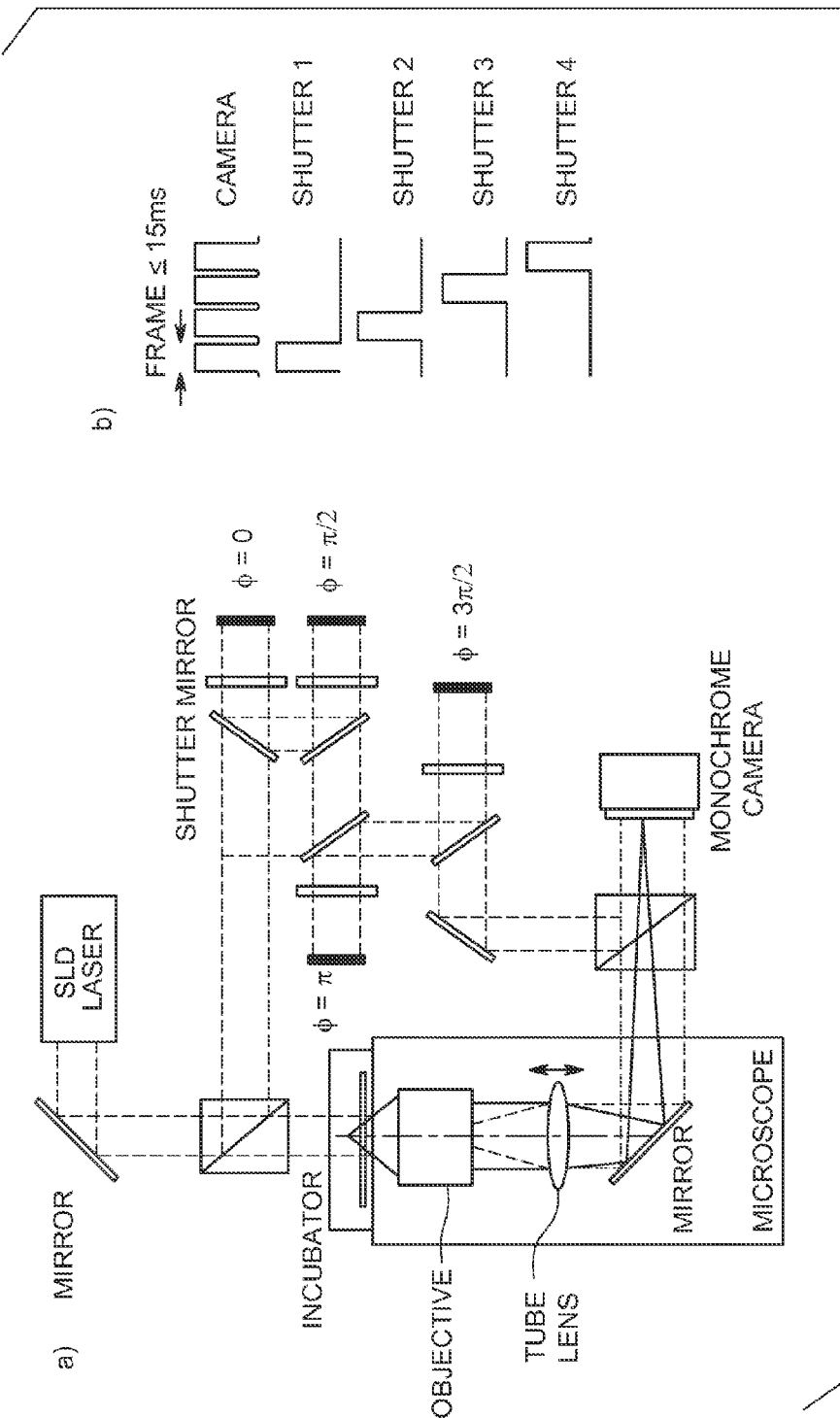
FIG. 24 schematically depicts an exemplary quantitative phase microscopy system for phase-contrast imaging configured for time multiplexing, in accordance with certain aspects of the invention.

In certain aspects of this disclosure, a quantitative microcopy system is provided that is configured to sequentially capture images at a plurality of phase delays, including but not limited to four phase displays (e.g., zero, π/2, π, and 3π/2), wherein the system employs a novel time multiplexing method for the rapid, simultaneous, or nearly simultaneous display of an image from the plurality (e.g., four) of phase displays. An exemplary quantitative microscopy system is presented in FIG. 24 and provides one system in which the time multiplexing method can be accomplished. Such a configuration and method permit the display of quantitative phase microscopy images suitable for perception by the human eye, thereby allowing one of skill in the art to monitor dynamic cellular processes in a short time period, such as within tens of milliseconds of exposure time. A person of skill in the art would recognize that FIG. 24 merely provides one quantitative microscopy system in which the novel multiplexing time method may be used, but that the multiplexing time method may be used in numerous quantitative phase microscopy systems.

Without intending to be limited to a particular mechanism of action or a specific design of a quantitative phase microscopy system, in one embodiment, the quantitative phase microscopy system will be configured to sequentially capture images at four phase delays, particularly zero, π/2, π, and 3π/2. Image acquisition may be accomplished by, for example, a monochrome CCD camera, like the Dalsa CMOS, which will enable image acquisition at appropriate lateral resolutions. The system will comprise a plurality of devices designed to generate the sequential phase displays. In one aspect of this embodiment, a plurality of ultrafast shutters with total window times 1.5 milliseconds is used to generate the desired sequential phase delays. Electro-optical modulator may alternatively function as the device for generating the sequential phase displays. Ultrafast shutters and electro-optical modulators (EOM) are merely exemplary devices to generate the sequential phase displays and are not intended to limit the invention. One of skill in the art would appreciate that any device capable of generating the desired sequential phase displays may be used in the practice of the invention.

Real-time image acquisition in the spatial variations using quantitative phase microscopy will require near simultaneous image acquisition from a plurality (e.g., four) optical path lengths of the reference beam with a speed of at least 15 frames/sec to ensure that the human eye does not perceive flicker and to continuously monitor the position of, for example, cells. To achieve the desired real-time acquisition, the plurality of devices used to generate the sequential phase delays will be configured to be electronically synchronized to a detector, including but not limited to a camera or a sensor, wherein the former produces an image and the latter provides an intensity signal. In particular aspects, this synchronization will be achieved by employing a synchronization device, including but not limited to triggering a digital pulse generator with the output synchronization pulse of the camera or sensor.

The sensor acquisition will be stopped and started from the PC; thus automatically synchronized with the shutters/EOM. The stop and start time of each shutter is precisely aligned to ensure no bleed through to the opposing frames. Shutters/EOM accommodate TTL inputs and provide open/close control. Raw camera images will be acquired using PC with custom image acquisition software.

Figure 25:
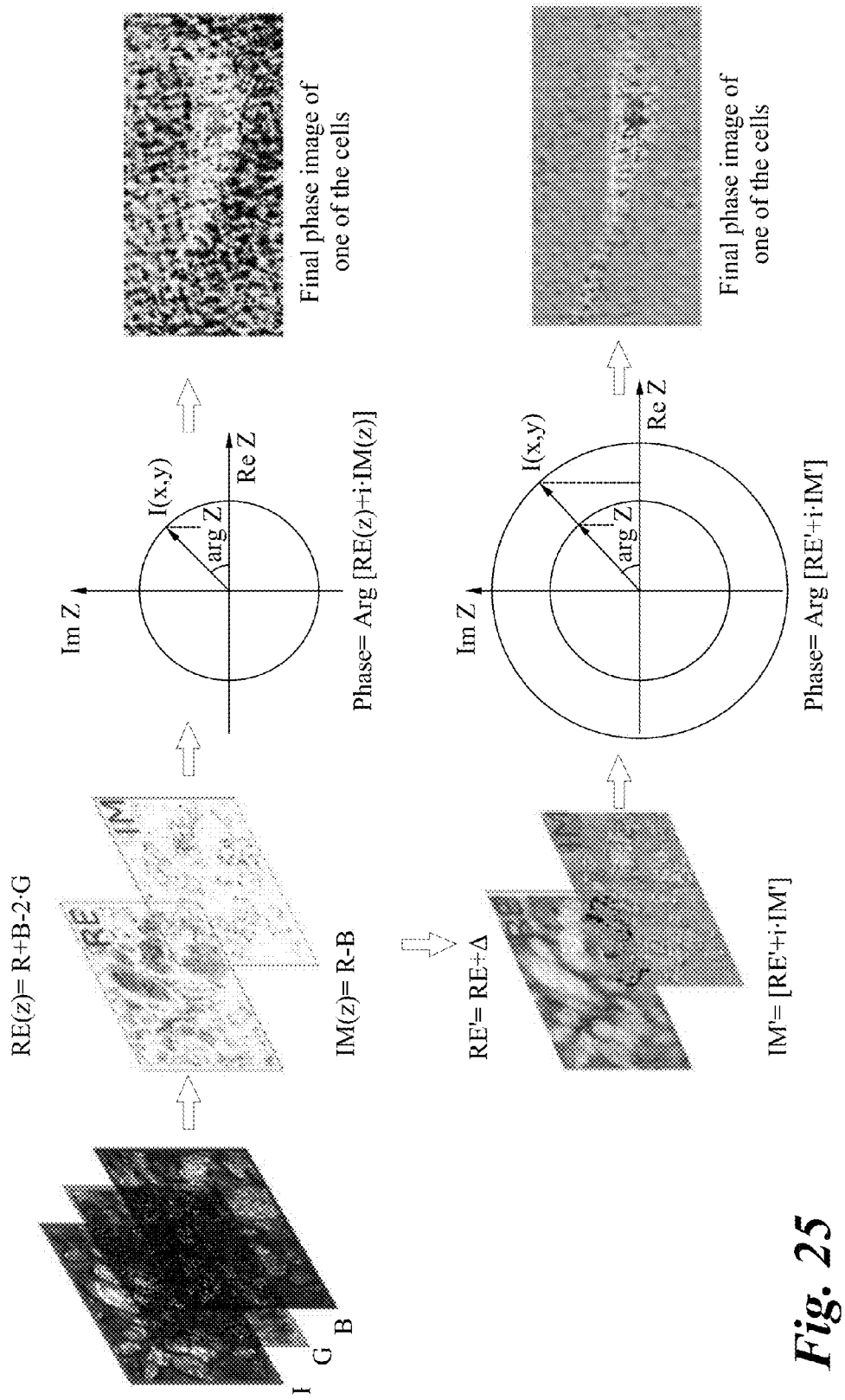
FIG. 25 provides the conventional algorithm for phase retrieval and the resultant image obtained, and the novel algorithm for phase retrieval disclosed herein and the resultant image, which displays the background noise suppression and the "speckle-free" background achieved by application of the novel algorithm described here.

The quality of the image obtained by quantitative phase microscopy may be also be improved by the application of a novel stretch algorithm that leads to reduction in background noise or "speckles." The conventional algorithm for phase retrieval and the images obtained by the application of this algorithm are presented in FIG. 25. The improved images obtained using the novel algorithm for phase retrieval developed herein are both set forth in FIG. 26. The developed algorithm can be applied towards images obtained both in quantitative phase microscope and in fluorescence microscope, combined with QPM.

Mathematical form of the equation (6 and/or 7) (i.e., periodic function with various poles in complex plane) may contribute to divergence of the phase calculation, effectively creating a "speckle" on the image (e.g., when denominator of Eq. (6 and/or 7) approaches zero). As such, special numerical evaluations of the fraction's numerator and denominator are needed to achieve a speckle-free image. The algorithm that guaranties uniform background of the phase image involves the following steps: 1) the image should be converted to float format; 2) an auxiliary complex variable Z=Re+i*Im should be calculated, where Re is the numerator of the fraction, and Im is it's denominator. The "speckled" phase is then simply equal to Arg(Z) (argument of the auxiliary variable). 3) A denominator shift Δ should be calculated based on the minimum pixel value in the "speckled" phase 2D pixel array. 4) A "stretched" auxiliary variable Zs should be introduced as $$Zs=[Re+\Delta \cdot tg\Delta\varphi]+i\cdot[Im+\Delta]. \tag{8}$$

The stretching performed this way ensures that the phase of the initial image is equal to the phase of the stretched image (since Arg(Z)=Arg(Zs)); however, any pixel with denominator's value in the proximity of zero, will be shifted by Δ, effectively eliminating the speckle. 5) The final phase image should be calculated as argument of the stretched variable Zs. 6) The float image should be converted to the original format (jpg, tiff, RGB, etc. . . . ) and displayed to the user. The entire algorithm is nearly instantaneous (limited only by computer's computational specs), which allows real-time elimination of speckled phase backgrounds.

Figure 26:
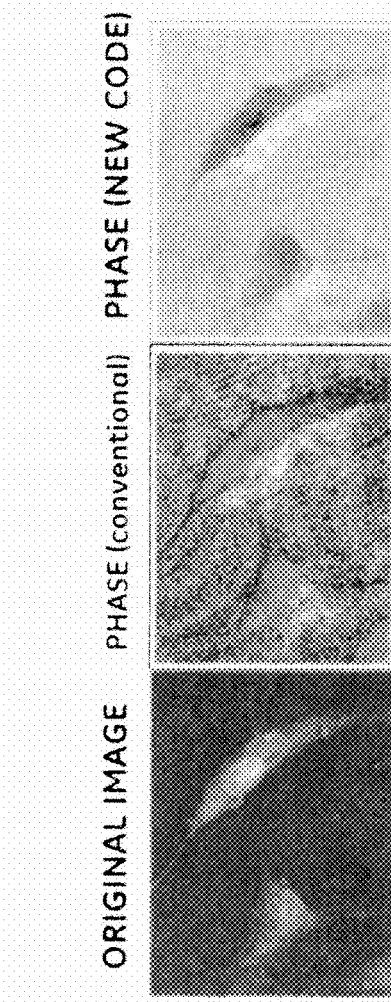
FIG. 26 provides the original image and the image obtained utilizing the conventional algorithm set forth in FIG. 25 and the novel algorithm disclosed herein. Better image quality and cell contrast are obtained when the novel algorithm is applied to the image data.

FIG. 26 provides automated real-time acquisition to display raw RGB image from the sensor (a), phase algorithm from eq. (6) (b), and novel algorithm from eq. 8 (c).

Example System and Method

The inventors have designed and constructed an example system similar to system 10 depicted in FIG. 1. The example system uses an 840 nm wavelength super luminescence laser diode, which has a coherence length of 6 μm, to illuminate samples. A transmission microscope including an objective and a tube lens was used to collect light diffracted by the samples and light not diffracted by the samples. The system used two cube beam splitters. Along a first path, the system included a first lens having a focal length of 60 mm and a second lens having a focal length of 60 mm. At the focal plane of the first lens, the system included a mask having an aperture with a diameter of 15 μm that transmitted most of the focused first undiffracted beam while blocking most of the first diffracted beam. Along a second path, the system included a third lens having a focal length of 150 μm and a fourth lens having a focal length of 150 μm. A moveable mirror was positioned on a piezoelectric transducer having a position resolution corresponding to 0.64 radians and a total range corresponding to 0 to 2π. The system included a high resolution CCD camera for obtaining 2-D images. In the description below, quantitative phase images are referred to as quantitative phase microscopy (QPM) images because a microscope is used for the collection of the diffracted and undiffracted light and the scale of the area imaged. In the description below and corresponding FIGS. 6, 8-15, 17, and 18-23, all QPM images are produced using a 4-step technique involving measurement of phase-contrast images at zero, π/2, π and 3π/2 relative phase shifts.

Example Results for Etched Step in Glass Sample

A glass sample having a step etched into it was measured with the example system. The step was independently measured to be about 218 nm in height using a Dektek Surface Profilometer. The QPM image 200 in FIG. 6 was generated from four measured phase-contrast images of the glass sample. In the area indicated by the rectangle 202, intensity values were averaged for reach row to provide average phase (in radians) as a function of x (in microns), which is displayed as trace 206 in graph 204. The phase difference of the step $\Delta\phi_{step}$ is about equal to 0.76 radians. The phase difference can be related to a height difference using the following formula in which Δh(x,y) is the relative height at a location, $\lambda_0$ is the central wavelength of the light source, and n(x,y) is the index of refraction of sample material at the location.

$$\Delta h(x, y) = \frac{\lambda_0}{2\pi(n(x, y) + 1)} \Delta\varphi(x, y) \quad (8)$$

For the glass sample, n is a constant value of 0.52, yielding a thickness value of 203 nm for the step, which is within 7% of the value measured with the Dektak Surface Profilometer. This agreement demonstrates that the example system and method can be used to obtain quantitative thickness information regarding a sample at the nanometer scale.

For biological samples, the index of refraction may be approximately constant across different locations, or it may vary for different types of cells or cellular structures (e.g., nuclei, organelles, cell walls) at each location. For example, the index of refraction of different biological samples may vary, at least, over a range of 1.33 to 1.47. In samples having a large variation in index of refraction, a determination of thickness may require use of an index of refraction that varies by location (x,y). One of ordinary skill in the art will appreciate that known values for indices of refraction for various cells and cellular structures may be used to calculate thickness values from quantitative phase values.

Example Results for Human Epithelial Cheek Cells

Figure 8:
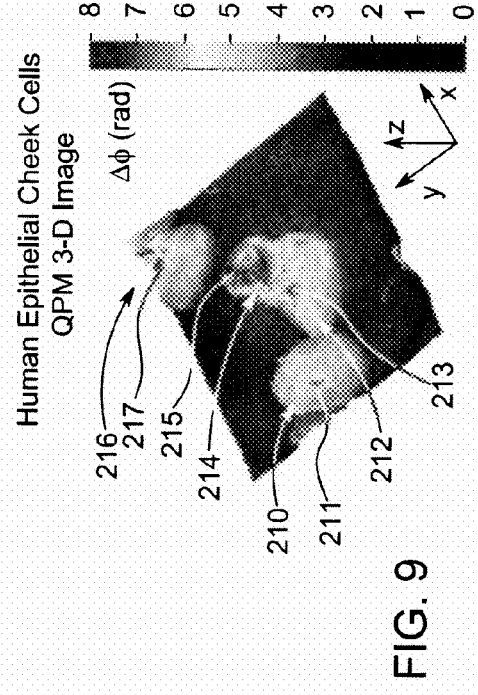
FIG. 8 is a two-dimensional image of a first set of quantitative phase microscopy data of human epithelial cheek cells obtained using the example system and method.
Figure 10:
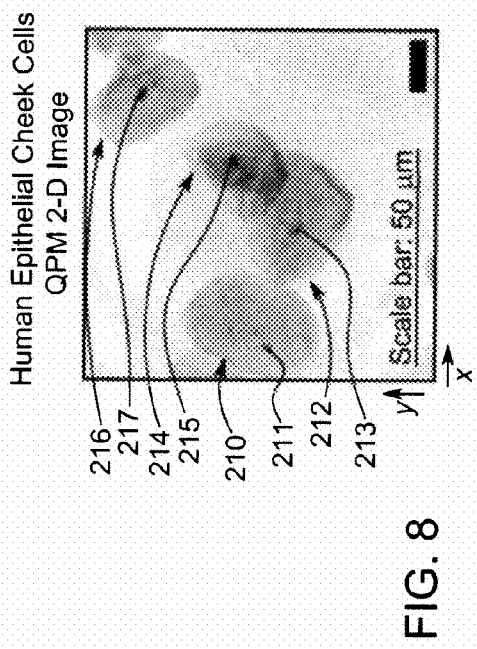
FIG. 10 is a two-dimensional image of a second set of quantitative phase microscopy data of human epithelial cheek cells obtained using the example system and method.
Figure 9:
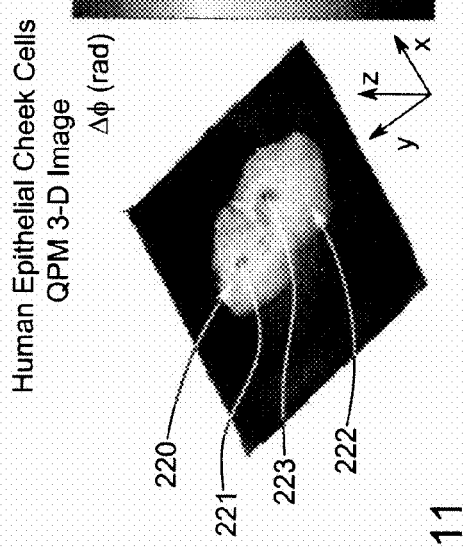
FIG. 9 is a perspective view of a three-dimensional image of the first set of quantitative phase microscopy data of human epithelial cheek cells with the relative phase displayed in the z-direction.
Figure 11:
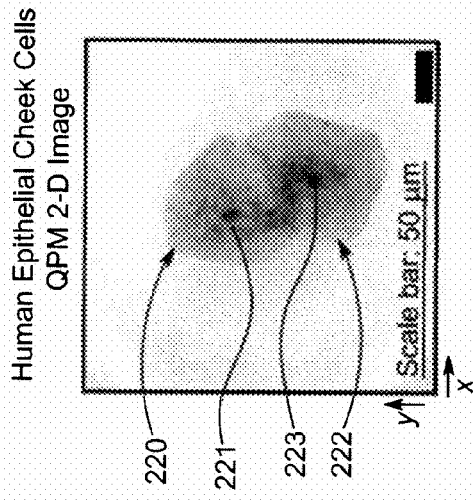
FIG. 11 is a perspective view of a three-dimensional image of the second set of quantitative phase microscopy data of human epithelial cheek cells with the relative phase displayed in the z-direction.
Figure 12:
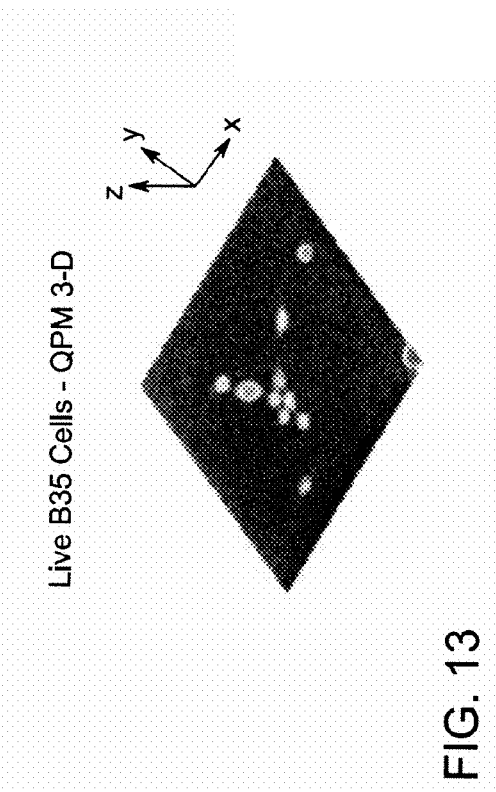
FIG. 12 is a two-dimensional image of a first set of quantitative phase microscopy data of live B35 cells in an imaging chamber obtained using the example system and method.

FIGS. 8-11 show QPM images of Human Epithelial Cheek Cells obtained using the example system described above. The Human Epithelial Cheek Cells were imaged while on a cover slip. As illustrated by FIG. 8, in which quantitative phase information is indicated by the image intensity at each location, the QPM image provides sufficient contrast to differentiate epithelial cheek cells 210, 212, 214, and 216 for segmentation. Further, the QPM image provides sufficient contrast to identify sub-cellular structures, such as nuclei 211, 213, 215, and 217. FIG. 9 includes a perspective view of a three-dimensional representation of the quantitative phase information appearing in FIG. 8, in which the phase is identified both by intensity and by height in the z-direction. FIG. 10 includes another two-dimensional QPM image of Human Epithelial check cells. FIG. 11 is a perspective view of a three-dimensional representation of the QPM information shown in FIG. 10. Although FIGS. 8 through 11 are in grayscale, in some embodiments, different colors may be used to indicate different phase values.

Example Results for B35 Cells

Figure 13:
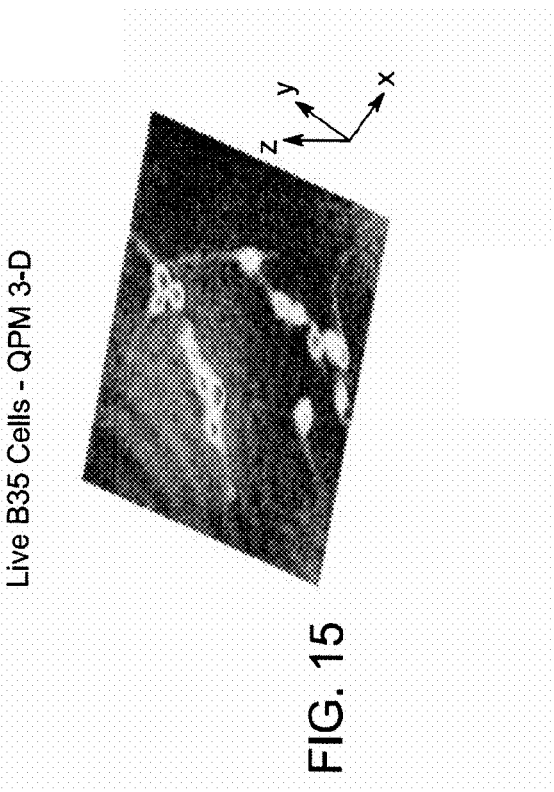
FIG. 13 is a perspective view of a three-dimensional image of the first set of quantitative phase microscopy data of live B35 cells in an imaging chamber with the relative phase displayed in the z-direction.
Figure 14:
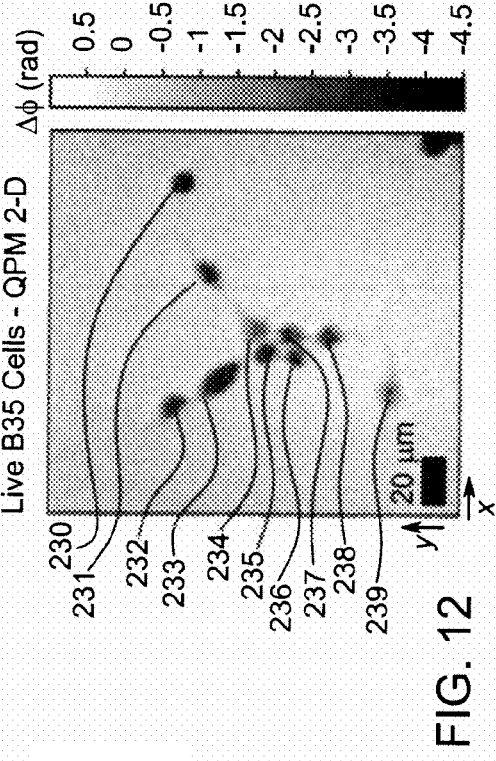
FIG. 14 is a two-dimensional image of a second set of quantitative phase microscopy data of live B35 cells in an imaging chamber obtained using the example system and method.
Figure 15:
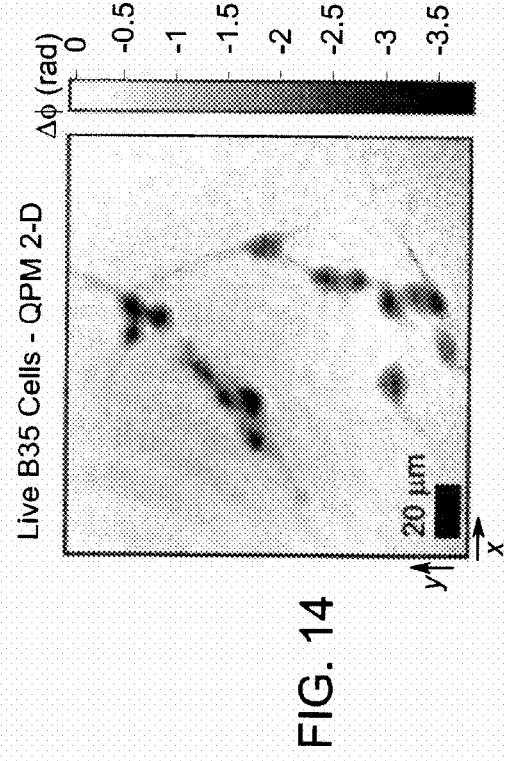
FIG. 15 is a perspective view of a three-dimensional image of the second set of quantitative phase microscopy data of live B35 cells in an imaging chamber with the relative phase displayed in the z-direction.

FIGS. 12-15 show QPM images of live B36 cells obtained using the example system described above. The B35 cell line is a neuronal cell line derived from tumors of the neonatal rat central nervous system. The live B35 cells were imaged while in an imaging chamber. As shown by the two-dimensional image in FIG. 12, in which quantitative phase information is indicated by the image intensity at each location, the QPM image provides sufficient contrast to differentiate B35 cells 230-239 for segmentation. FIG. 13 includes a perspective view of a three-dimensional representation of the quantitative phase information appearing in FIG. 12, in which the phase is identified both by intensity and by height in the z-direction. FIG. 14 includes another two-dimensional QPM image of live B35 cells, and FIG. 15 is the corresponding perspective view of a three-dimensional representation of the QPM image.

Example Results for Gut Tissue Section

Figures 16, 17:
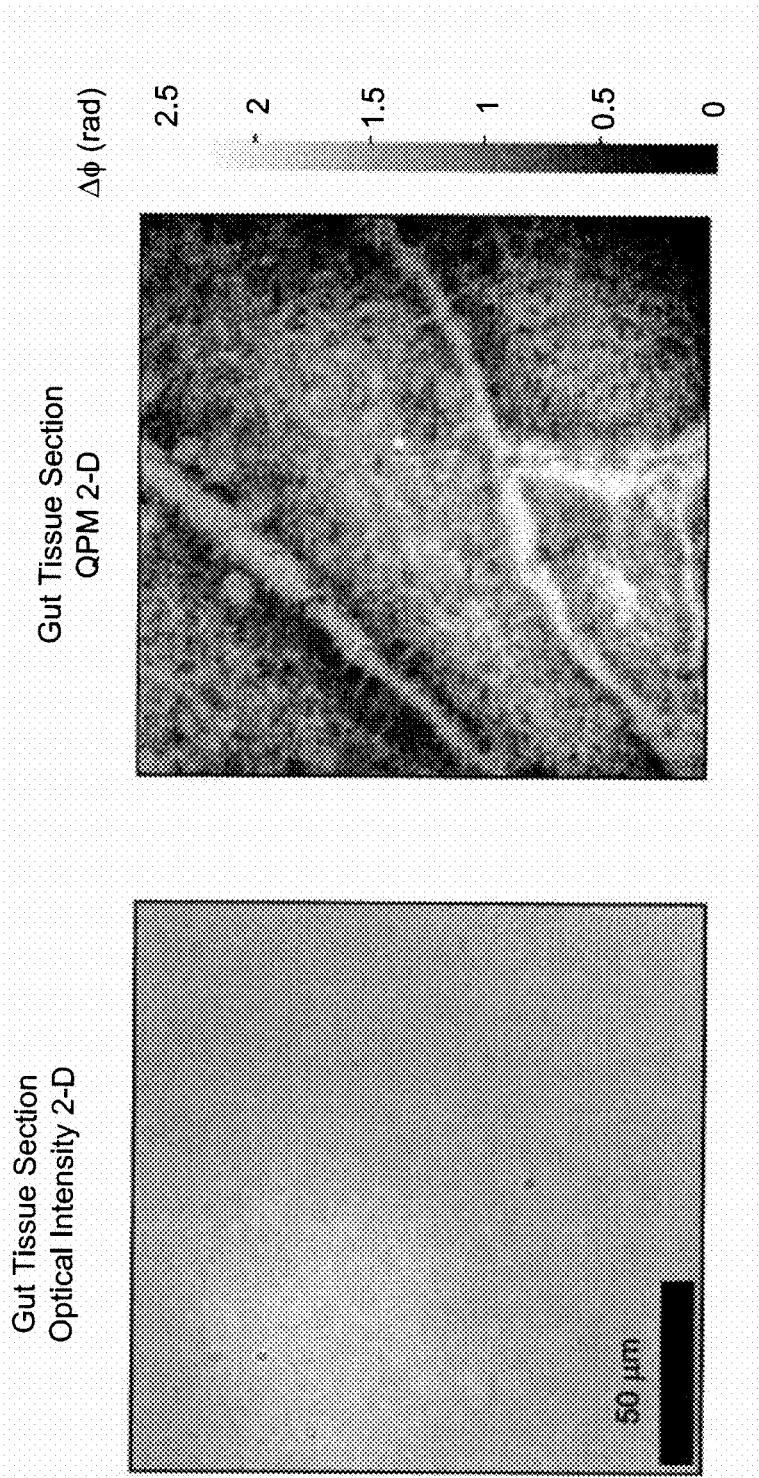
FIG. 16 is a two-dimensional optical intensity image of a thin gut tissue section sample.
FIG. 17 is a two-dimensional image of a first set of quantitative phase microscopy data of the thin gut tissue section sample produced from phase-contrast images obtained using the example system and method.

FIGS. 16-20 are images of a thin gut tissue section sample. FIG. 17 is a two-dimensional QPM image of the tissue section sample. FIG. 16 is an optical intensity image of the same spot in the tissue section sample for comparison purposes. As illustrated by FIGS. 16 and 17, the QPM image of the gut tissue section in FIG. 17 provides superior image resolution and superior image contrast as compared with the optical image in FIG. 16. Further, QPM image also provides quantitative phase information.

FIGS. 18-20 include QPM images of a gut tissue section sample produced from phase-contrast images taken with the example system configured for different magnifications. FIG. 18 includes a QPM image of a thin gut tissue section produced from phase-contrast images obtained using a microscope with an Olympus YPlanFL 4×/0.13 objective (plan, fluorite, magnification 4×, numerical aperture 0.13). FIG. 19 includes a QPM image of a thin gut tissue section produced from phase-contrast images obtained using a microscope with an Olympus YPlanFL 20×/0.5 objective (plan, fluorite, magnification 20×, numerical aperture 0.5). FIG. 20 includes a QPM image of a thin gut tissue section produced from phase-contrast images obtained using a microscope with an Olympus UPlanSApo 40×/0.95 objective (plan, achromat, magnification 40×, numerical aperture 0.95). As shown by FIGS. 19 and 20, even under relatively high magnification, 20× and 40× respectively, the QPM images show good resolution and good image contrast.

Example Results for Rat Mesenchymal Stem Cells

Figures 21, 22, 23:
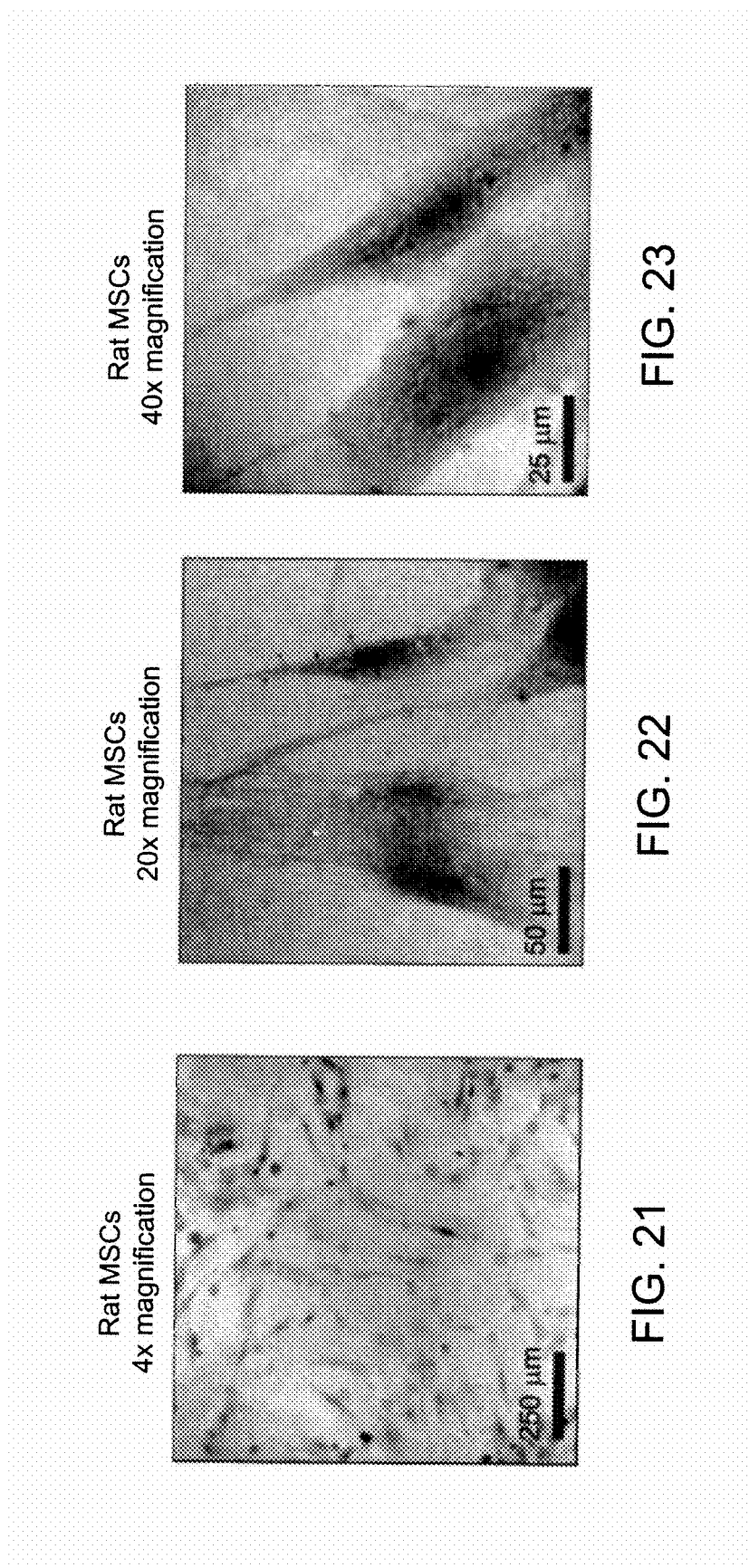
FIG. 21 is a two-dimensional image of a first set of quantitative phase microscopy data of a rat mesenchymal stem cell sample obtained using the example system and method with a microscope configured for 4× magnification.
FIG. 22 is a two-dimensional image of a second set of quantitative phase microscopy data of the rat mesenchymal stem cell sample obtained with the microscope configured for 20× magnification.
FIG. 23 is a grayscale two-dimensional image of a third set of quantitative phase microscopy data of the rat mesenchymal stem cell sample obtained with the microscopy configured for 40× magnification.

FIGS. 21-23 include QPM images of a sample of rat mesenchymal stem cells (MSCs) produced from phase-contrast images taken with the example system configured for different magnifications. The rat MSCs were imaged while on a cover slip. MSCs are multipotent stem cells, which are derived from the bone marrow of rats, and can differentiate into a variety of cell types. FIG. 21 includes a QPM image of the MSCs produced from phase-contrast images obtained using the example system with the Olympus YPlanFL 4×/0.13 objective (plan, fluorite, magnification 4×, numerical aperture 0.13) in the microscope. FIG. 21 includes a QPM image of the MSCs produced from phase-contrast images obtained with the Olympus YPlanFL 20×/0.5 objective (plan, fluorite, magnification 20×, numerical aperture 0.5). FIG. 22 includes a QPM image of the MSCs produced from phase-contrast images obtained with the Olympus UPlanSApo 40×/0.95 objective (plan, achromat, magnification 40×, numerical aperture 0.95). As shown by FIGS. 22 and 23, even under relatively high magnification, 20× and 40× respectively, the QPM images of MSCs show good resolution and high image contrast.

While some features of embodiments of the invention have been illustrated and described herein, many modifications and changes will be clear to those of skill in the art based on this application. It is, therefore, to be understood that the appended claims are intended to cover all such modifications and changes as fall within the true spirit of the invention.

Although the claims recite specific combinations of limitations, the invention expressly encompasses each independent claim by itself and also in conjunction with any possible combination of limitations articulated in the related dependent claims except those that are clearly incompatible.

The invention claimed is:

1. A system for phase contrast imaging of a sample comprising:
   a light source for illuminating the sample, wherein a first beam splitter generates from the light source at least a first beam of light and a second beam of light, wherein a first optical element is configured to collect light from the first beam of light that is not diffracted by the sample, and wherein a second optical element is configured to collect light from the second beam of light that is diffracted by the sample and that is not diffracted by the sample;
   a plurality of devices used to generate a sequential phase delay, wherein the first beam of light is split into a plurality of phase delays by passage through the plurality of devices used to generate the sequential phase delay;
   a second beam splitter positioned to collect the light from the sample and undiffracted reference beam;
   a detector that collects the light from the first beam of light after passage through the plurality of devices used to generate the sequential phase delay and further collects the light from the second beam of light later after passage through the sample; and
   a synchronization device configured to synchronize the plurality of devices to the detector, wherein the synchronization device is a pulse generator.

2. The system of claim 1, wherein the plurality of phase delays comprises zero, $\pi/2$, $\pi$, and $3\pi/2$.

3. The system of claim 1, wherein the system is configured for label-free, high-contrast imaging of samples including one or more cells.

4. The system of claim 1, wherein the system is configured for label-free, high-contrast imaging of dynamic biological processes in tens of milliseconds.

5. The system of claim 4, wherein the dynamic biological process is cardiac cell contraction or nervous system model stretching.

6. The system of claim 1, wherein the light source for illuminating the sample produces a beam of light with a coherence length that is less than 10 microns.

7. The system of claim 1, wherein the first optical element or the second optical element comprises a microscope objective.

8. The system of claim 1, wherein first optical element or the second optical element comprises a tube lens.

9. The system of claim 1, wherein the plurality of devices used to generate a sequential phase delay comprise ultrafast shutters or electro-optical modulators.

10. The system of claim 1, wherein the detector is a camera or a sensor.

11. A method for quantitative phase imaging of a sample, the method comprising:
    a) providing a light source for illuminating the sample, wherein a first beam splitter generates from the light source at least a first beam of light and a second beam of light, wherein a first optical element is configured to collect light from the first beam of light that is not diffracted by the sample, and wherein a second optical element is configured to collect light from the second beam of light that is diffracted by the sample and that is not diffracted by the sample;
    b) splitting the first beam of light into a plurality of sequential phase delays by passage through a plurality of devices
    c) collecting, by a detector, the light from the first beam of light after passage through the plurality of devices and the light from the second beam of light later after passage through the sample; and
    d) electronically synchronizing the plurality of devices with the detector to produce a quantitative phase image.

12. The method of claim 11, wherein the plurality of phase delays comprise zero, $\pi/2$, $\pi$, and $3\pi/2$.

13. The method of claim 11, wherein the sample includes one or more cells and the quantitative phase image comprises a label-free, high-contrast image of the sample.

14. The method of claim 11, wherein the plurality of devices comprises at least one ultrafast shutter or at least one electro-optical modulator.

15. The method of claim 11, wherein the detector is a camera or a sensor.

16. The method of claim 11, wherein the method further comprises performing label-free automated segmentation of cells and/or nuclei based on the quantitative phase image.

17. The method of claim 11, wherein the method further comprises near simultaneous display of the sequential phase delays.

18. The method of claim 11, wherein the method further comprises label-free, high-contrast imaging of dynamic biological processes in tens of milliseconds.

19. The method of claim 18, wherein the sample includes a cell monolayer, and wherein the method further comprises generating quantitative thickness information regarding the sample based on at least a portion of the quantitative phase image of the sample.

20. The method of claim 11, further comprising generating quantitative thickness information for each location in at least a portion of the quantitative phase image based on at least a part of the portion of the quantitative phase image.

\* \* \* \* \*